(12) United States Patent
Rao et al.

(10) Patent No.: US 7,238,839 B2
(45) Date of Patent: Jul. 3, 2007

(54) PROCESS FOR THE RESOLUTION OF RACEMIC (R,S) -5-(2-(2-(2-ETHOXYPHENOXY)ETHYLAMINO)PROPYL)-2-METHOXYBENZENE SULFONAMIDE (TAMSULOSIN), ITS NOVEL R AND S ISOMERS AND THEIR SALTS AND PROCESSES FOR THEIR PREPARATION

(75) Inventors: Bolineni Nageswara Rao, Hyderabad (IN); Mutyala Krishnaji Rao, Hyderabad (IN); Allupati Padmanav Patro, Hyderabad (IN); Ambadipudi Udayalakshmi, Hyderabad (IN); Mutyala Veeraiah, Hyderabad (IN); Gundu Rao Padakandala, Hyderabad (IN)

(73) Assignee: Divi's Laboratories Limited (IN)

( * ) Notice: Subject to any disclaimer, the term of this patent is extended or adjusted under 35 U.S.C. 154(b) by 164 days.

(21) Appl. No.: 11/136,051

(22) Filed: May 24, 2005

(65) Prior Publication Data

US 2006/0079714 A1   Apr. 13, 2006

(30) Foreign Application Priority Data

Oct. 7, 2004  (IN) .................. 1033/CHE/2004

(51) Int. Cl.
*C07C 311/30* (2006.01)
(52) U.S. Cl. ...................................... 564/86
(58) Field of Classification Search .............. None
See application file for complete search history.

(56) References Cited

U.S. PATENT DOCUMENTS

| | | | |
|---|---|---|---|
| 4,373,106 A | 2/1983 | Imai et al. | |
| 4,703,063 A | 10/1987 | Imai et al. | |
| 4,731,478 A | 3/1988 | Niigate et al. | |
| 4,772,475 A | 9/1988 | Fukui et al. | |
| 4,868,216 A | 9/1989 | Imai et al. | |
| 5,391,825 A | 2/1995 | Niigata et al. | |
| 5,447,958 A | 9/1995 | Niigata et al. | |
| 2003/0109752 A1 | 6/2003 | Hoorn et al. | |

FOREIGN PATENT DOCUMENTS

| | | |
|---|---|---|
| EP | 0034432 A2 | 8/1981 |
| EP | 0257787 A1 | 3/1988 |
| WO | WO 03/035608 A1 | 5/2003 |
| WO | WO 03/037850 A1 | 5/2003 |

OTHER PUBLICATIONS

Honda, C., J. Pharm. Exp. Therap. 239, 512 (1986).
Jacques et al., Enantiomers, Racemates and Resolutions, Chap. 5, pp. 251-261, Krieger Publishing Company (1994).

*Primary Examiner*—Thurman K. Page
*Assistant Examiner*—Valenrod Yevgeny
(74) *Attorney, Agent, or Firm*—Caesar, Rivise, Bernstein, Cohen & Pokotilow, Ltd.

(57) ABSTRACT

An improved process is described to resolve a racemic mixture in any proportion of 5-(2-(2-(2-ethoxyphenoxy)ethylamino)propyl)-2-methoxy benzene sulfonamide as a free base or some of its salts, with BPA either S or R form to obtain enantiomerically highly pure R and S-isomer as a well characterized free base or as a salt of the title compound. Also described are novel R and S-isomers of 5-(2-(2-(2-ethoxyphenoxy) ethylamino)propyl)-2-methoxy benzene sulfonamide and their salts and the processes for their preparation.

20 Claims, 18 Drawing Sheets

PROCESS FOR THE RESOLUTION OF RACEMIC (R,S) -5-(2-(2-(2-ETHOXYPHENOXY) ETHYLAMINO)PROPYL)-2-METHOXYBENZENE SULFONAMIDE (TAMSULOSIN), ITS NOVEL R AND S ISOMERS AND THEIR SALTS AND PROCESSES FOR THEIR PREPARATION

BACKGROUND OF THE INVENTION

1. Field of Invention

This invention relates to an improved process of resolving a racemic mixture of 5-(2-(2-(2-ethoxyphenoxy) ethylamino) propyl)-2-methoxy benzene sulfonamide, commonly known as tamsulosin. This invention also relates to novel R and S isomers of 5-(2-(2-(2-ethoxyphenoxy)ethylamino)propyl)-2-methoxybenzene sulfonamide and their salts and processes for their preparation.

2. Description of Related Art

The compound tamsulosin (Structure I, below) is a new type of highly selective α-adrenoceptor antagonist, clinically useful for patients with urinary obstruction due to benign prostatic hyperplasia (BPH) and in cardiac insufficiency. The racemic compound and its applications are revealed in the European Patent No. 0034432, U.S. Pat. Nos. 4,373,106 and 4,868,216. Although there is a chiral center in the molecule (indicated by a star in Structure I), none of these patents disclose the existence of the optical isomers.

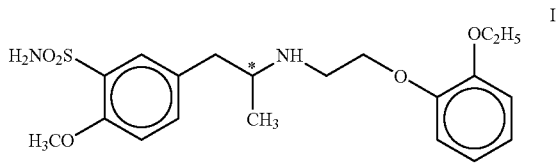

U.S. Pat. No. 4,772,475 discloses a controlled release formulation using racemic tamsulosin as the active ingredient. In all of these patents, only the tamsulosin hydrochloride salt has been considered for therapeutic applications.

U.S. Published Patent Application No. 2003/0109752 and WO 03/037850 disclose methods of obtaining solid racemic tamsulosin base in two polymorphic forms.

U.S. Pat. No. 4,703,063 discloses several "sulfamoyl-substituted phenethylamine derivatives" represented by a general formula in claim 1. Dependent claim 6 discloses racemic compounds of all of the analogs of claim 1. Similarly, claims 8 to 10 disclose all optically active compounds of claim 1. Claim 14 discloses the chemical name of tamsulosin, without mentioning the optical isomer. This racemic compound is described in example 20 only as its hydrochloride. As per example 20 and the scheme of its preparation in column 26 of the body of the patent, this compound was prepared by a non-stereospecific route resulting in a racemic compound only. There is neither a method of resolution nor a stereospecific synthetic route described for any compound claimed in the '063 patent.

U.S. Pat. No. 4,731,478 discloses the optical isomers of tamsulosin, but biological activity of only the (−) isomeric form is revealed. The two Examples, namely 33(a) and 33(b), describe a method of stereospecific synthesis of the optical isomers.

The stereospecific synthesis consists of condensing a chirally active intermediate amine, (R)(−)isomer as in Example 33(a) or (S)(+)isomer as in Example 33(b), with the achiral bromo intermediate to yield the corresponding chiral base and converting the same to its hydrochloride salt. Although the Example states that "crude crystals of (R)(−)-5-[2[2-(o-ethoxy phenoxy)ethylamino]-2-methylethyl]-2-methoxy benzene sulfonamide" were obtained, this base was not characterized further but converted to its salt, namely the hydrochloride. The hydrochloride was characterized only with its melting point, elemental analysis and optical rotation. Although the claims are exclusively for the optically active tamsulosin base (not the hydrochloride form) and specifically for (−) isomer of tamsulosin base (not the hydrochloride form), there is neither an Example nor a process described or suggested for the preparation of the pure "optically active" tamsulosin base. No characteristics of the "optically active" tamsulosin base are given anywhere in this patent or related patents by the same inventors. Even the specific optical rotation of the claimed (−)tamsulosin free base is not disclosed.

It is therefore believed that the applicants of the '478 patent failed to actually isolate and characterize the pure free bases of the two enantiomers of tamsulosin. No process for resolution of the racemic tamsulosin is shown or suggested in the '478 patent.

European Patent No. 02/57787 describes in Example 4 the preparation of (R)-tamsulosin by condensing the chiral intermediate R(−)5-(2-aminopropyl)-2-methoxy benzene sulfonamide, with the achiral intermediate 2-(2-ethoxyphenoxy)-ethyl bromide exactly as described in the U.S. Pat. No. 4,731,478. The same stereospecific synthetic process is also disclosed. However, there is no mention of any resolution process for the racemic compound.

U.S. Pat. No. 5,391,825 is similar to U.S. Pat. No. 4,731,478 in several aspects. Examples 33(a) and 33(b) in both patents reveal a method of preparing the optically active isomers as hydrochlorides by a synthesis using the appropriate chiral intermediate. However, the claims are limited to the achiral intermediate only. U.S. Pat. No. 5,447,958 claims the (R) tamsulosin as a compound and its application in pharmaceutical compositions. The method of its preparation as hydrochloride is given in Example 33(a) by synthesis using the chiral intermediate as in other U.S. patents cited earlier.

WO Patent No 03/035608 describes the same synthetic route to the (R) tamsulosin as a hydrochloride, however by improved conditions of reaction. In none of these patents is there shown a resolution process for obtaining the required (R) isomer from its racemic form. None of these patents discloses the characteristics of the free bases. It is thus believed that the pure R & S isomers were never isolated.

Although none of the patents mentioned above provide any biological data supporting the use of the (R) isomer in preference to the racemic form, the publication by Honda. K. and Nakagawa, C. in J. Pharm. Exp. Therap. 239, 512 (1986) suggests the advantage of the (R) isomer over the (S) isomer and the racemic form of tamsulosin.

U.S. Published Patent Application No. 2003/0109752 and its counterpart WO 03/037850 (PCT/NL02/00657) are applications disclosing means for resolving a racemic mixture of tamsulosin base. The racemic free base may be obtained directly by synthesis or the racemic salt may be converted to free racemic base followed by partial purification as camphor sulfonate addition salt, which is enriched in the 'R'-isomer. The scheme is outlined in Chart I shown below:

CHART 1

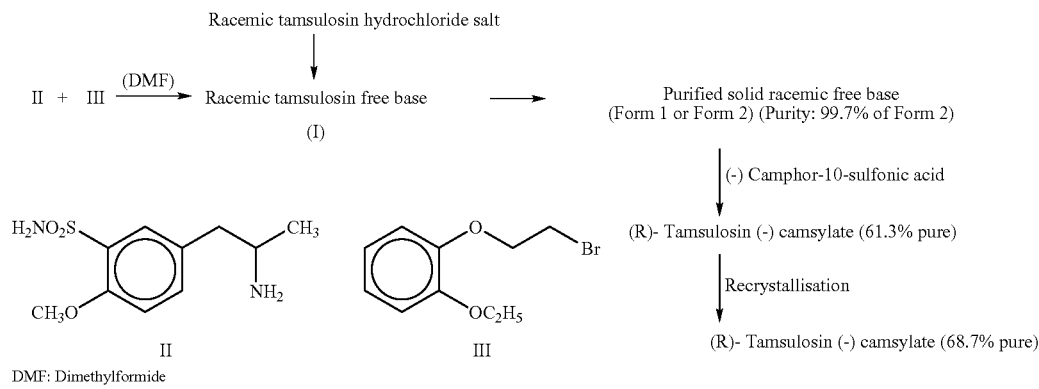

DMF: Dimethylformide

The purity of the (R) isomer is low (68.7%) even after recrystallization. The applicants have developed another process, which results in an isomer having an enantiomeric purity of over 99.5%. The process is outlined in the Chart 2 given below. The starting material is purified racemic tamsulosin free base obtained by one of the methods as outlined in Chart 1 shown above.

Thus, there is a great need for developing a commercially viable, less tedious process of resolving racemic tamsulosin, which can be easily prepared by known methods, without resorting to chiral intermediates and stereospecific synthesis.

There is also a need for obtaining pure and well characterized R and S enantiomeric tamsulosin free bases. As the racemic mixture itself is being used in therapy since its

CHART 2

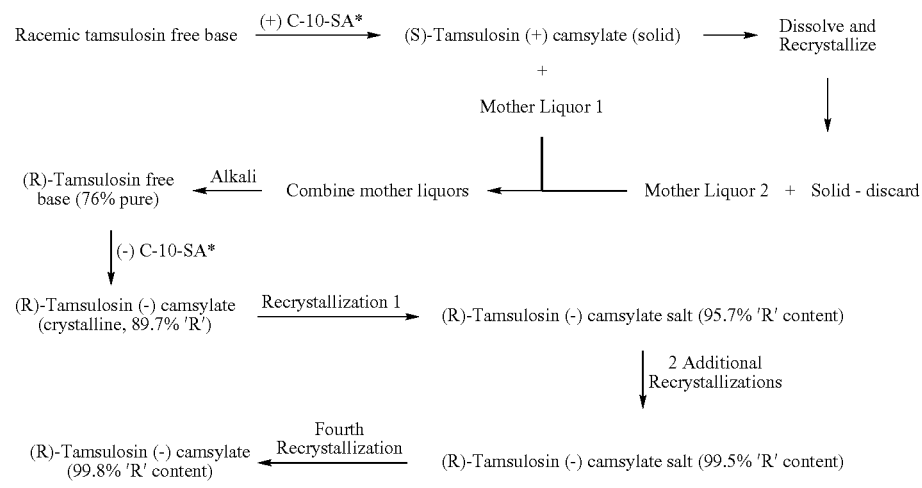

* C-10-SA = Camphor - 10 - sulfonic acid

The overall yield of the salt after four crystallizations was 47.4% based on the 76% purified free base. It is clear from the above that to obtain a purity of 99.5% for the (R) tamsulosin (−) camsylate salt itself, a very tedious process is required, which can then be converted to pure (R) tamsulosin by alkaline treatment.

According to WO 03/037850 at page 4, lines 3-4, prior to its publication, "no method was known as how to purify such an optically impure product (tamsulosin)." This patent application also failed to isolate free bases of the two enantiomers of tamsulosin and characterize them. It reveals only the solid form of racemic tamsulosin base, its application mainly for the resolution as described in the application.

launch, the presence of about 1% of the (S) isomer in the resolved and isolated (R) isomer does not adversely affect the improved activity of the (R) isomer. Moreover no adverse effects of the enriched (S) isomer are reported in literature. The pure isomers so obtained are excellent starting materials for conversion to optically pure salts other than the hydrochlorides.

All references cited herein are incorporated herein by reference in their entireties.

OBJECTIVES OF THE PRESENT INVENTION

Without being limiting in any fashion, it is one of the objectives of the present invention to provide an improved process for effectively resolving a mixture of (R) and (S) isomers of tamsulosin in any proportion, to obtain either of the isomers as free bases in an enantiomeric purity of at least 99%.

Another objective of the present invention is to provide an improved process for resolving the racemic mixture of (R) and (S) isomers of tamsulosin acid addition salts directly, by using the resolving agent which has not hitherto been used for the purpose.

Yet another objective of the present invention is to provide an improved process for the preparation of pharmaceutically acceptable acid addition salts of the resolved and isolated (R) and (S) isomers in a purity of greater than 99% enantiomeric excess.

Still another objective of the present invention is to provide novel isomers of tamsulosin free base and its salts.

Yet another objective of the present invention is to provide processes for the preparation of novel isomers of tamsulosin free base and its salts

BRIEF SUMMARY OF THE INVENTION

Tamsulosin is a secondary amine and exhibits basic properties forming salts with acids. The only report of partially successful resolution was achieved using optically active camphor-10-sulfonic acids, as explained earlier. Other commonly employed acids and their derivatives like tartaric acids, esters of tartaric acids, mandelic acids were tried in our search for a satisfactory resolving agent. We also tried the less common chirally pure R & S naproxens with no success. Finally it was possible to obtain satisfactory results by the use of R(−)-1,1'-binaphthyl-2,2'-diyl-hydrogen phosphate (CAS Registry No: 39648 -67-4), hereinafter simply designated as R-BPA, or S(+)-1,1'-binaphthyl-2,2'-diyl hydrogen phosphate (CAS Registry No. 35193-64-7), hereinafter simply designated as S-BPA, as resolving agents.

Accordingly, the present invention provides novel isomers of tamsulosin free base.

According to another feature of the invention there is provided novel salts of isomers of tamsulosin such as oxalic, fumaric, salicylic, maleic and tartaric acids.

According to yet another feature of the present invention there are provided processes for the preparation of novel salts of the isomers of tamsulosin such as oxalic, fumaric, salicylic, maleic and tartaric acids.

Accordingly, the present invention provides an improved process for the resolution of a mixture of (R) and (S) isomers of tamsulosin which comprises:
(i) mixing the racemic mixture of tamsulosin or its salts and S(+)BPA in an organic solvent or a mixture of an organic solvent and water;
(ii) maintaining the resulting mixture at a temperature in the range of about 20° to about 60° C. for a period in the range of about 2 to about 10 hours;
(iii) filtering the solid R-tamsulosin-S-BPA salt formed;
(iv) liberating the R-tamsulosin free base by basification and recovering the free base by filtration and work-up by conventional methods, and if desired;
(v) converting the R-tamsulosin free base so obtained to a pharmaceutically acceptable salt by conventional methods;
(vi) recovering the S-tamsulosin or its salt from the filtrate obtained in (iii) above by known methods; and
(vii) recovering the chiral resolving agent -(S)-BPA used from the mother liquors obtained in steps (iv) or (vi) by conventional methods.

According to another embodiment of the present invention there is provided an improved process for the resolution of a mixture of (R) and (S) isomers of tamsulosin which comprises:
(i) mixing the racemic mixture of tamsulosin or its salts and R(+)BPA in an organic solvent or a mixture of an organic solvent and water;
(ii) maintaining the resulting mixture at a temperature in the range of about 20° to about 60° C. for a period in the range of about 2 to about 10 hours;
(iii) filtering the solid S-tamsulosin-R-BPA salt formed;
(iv) liberating the S-tamsulosin free base by basification and recovering the free base by filtration and work-up by conventional methods, and if desired;
(v) converting the S-tamsulosin free base so obtained to a pharmaceutically acceptable salt by conventional methods;
(vi) recovering the R-tamsulosin or its salt from the filtrate in (iii) above; and
(vii) recovering the chiral resolving agent-(R)-BPA used in the process from the mother liquors obtained in steps (iv) or (vi) by conventional methods.

The chiral purity of the salt of R-tamsulosin-(S)-BPA prepared was found to be 96.88% (Chiral HPLC) with only 3.12% of the S-tamsulosin-(S)-BPA salt.

The R-tamsulosin-S-BPA salt is well characterized by recording IR, $^1$H-NMR, $^{31}$P-NMR, XRD spectroscopic data and DSC thermogram, besides the optical rotation.

The mother liquors obtained from both of the above-mentioned resolution processes contain one of the isomers enriched. Therefore, the mother liquors are treated with a base, usually ammonia, to liberate the free tamsulosin base (mixture of R or S isomer), which can be extracted into an organic solvent like ethyl acetate and recovered as a solid after distilling off the solvent. The resolving agent remains in the aqueous phase in a microfine suspension as ammonium salt and can be liberated by addition of a mineral acid like hydrochloric acid and completely recovered. The mixture of the R and S isomers of tamsulosin is further processed as in the initial resolution step by using the appropriate resolving agent, i.e., S-BPA to recover R-tamsulosin as a solid or R-BPA to recover S-tamsulosin as a solid.

BRIEF DESCRIPTION OF SEVERAL VIEWS OF THE DRAWINGS

The invention will be described in conjunction with the following drawings, wherein each of the drawings shows the following spectral analyses.

DETAILED DESCRIPTION OF PREFERRED EMBODIMENTS OF THE INVENTION

Figure 1:
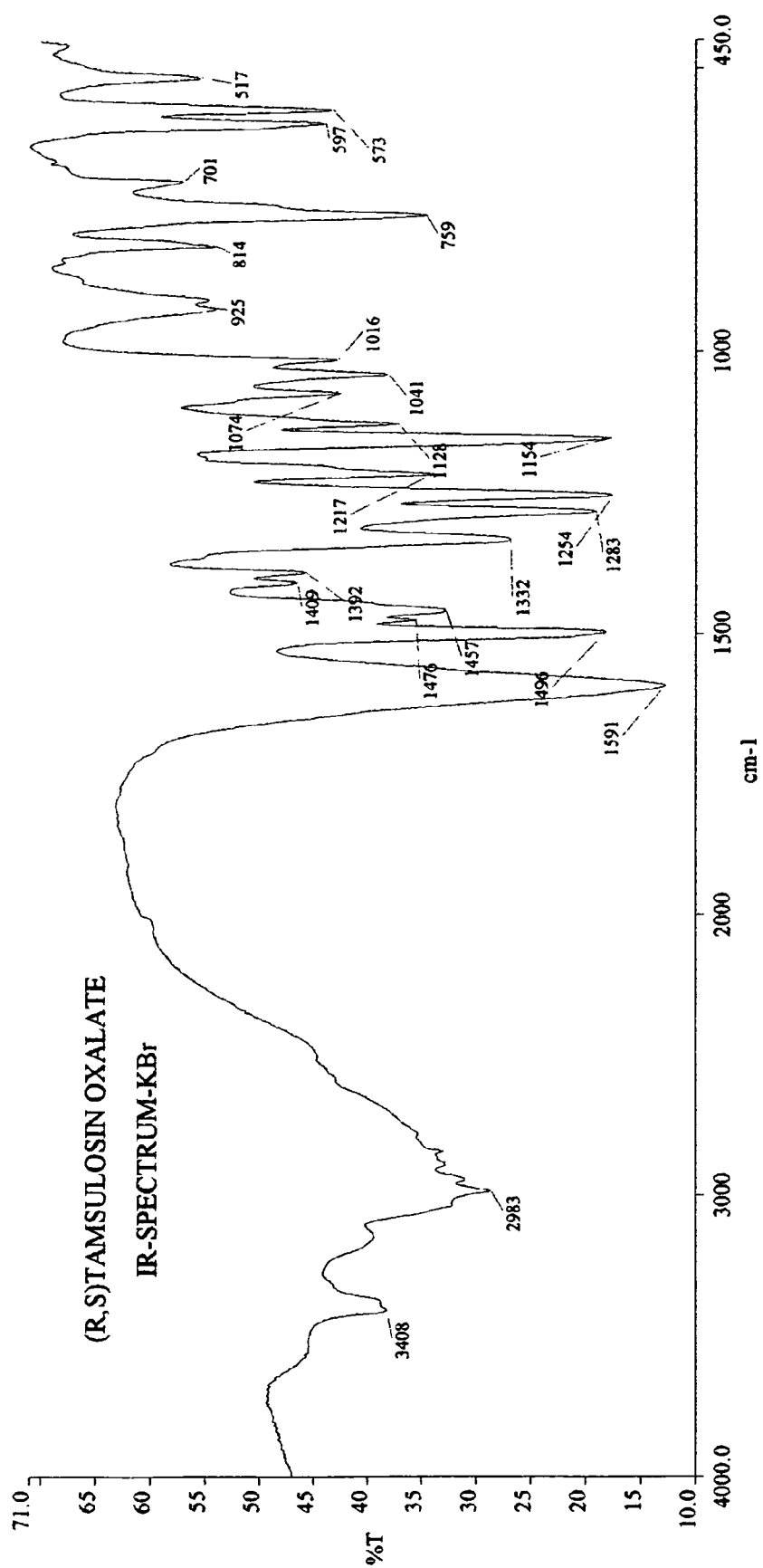
FIG. 1: (R,S)-Tamsulosin oxalate (IR-Spectrum-KBr).

Racemic salts of tamsulosin obtained by any suitable process may be used in the resolution process according to present invention. The circuitous route of synthesis as described in European Patent 34432 or its equivalent U.S. Pat. No. 4,703,063 or U.S. Pat. No. 4,731,478 result in the hydrochloride salt. The closely related analog, 2-methoxy-5-[2-[2-(2-methoxyphenoxy)ethylamino]methylethyl]-N-methyl-benzene sulfonamide hydrochloride revealed in Example 4 of U.S. Pat. No. 5,447,958, was synthesized by reductive amination of the appropriate ketone with the appropriate amine. This method is well suited for obtaining the salts of racemic tamsulosin also, by choosing the appropriate ketone and amine.

In this invention, the method as described in Example 4 of the U.S. Pat. No. 5,447,958 was adopted to prepare the salt of racemic tamsulosin. U.S. Published Application No. 2003/0109752 and its corresponding WO 03/037850 describe other methods of obtaining racemic tamsulosin free base, which can also be used in the present invention. We have found that either the racemic free base or acid addition salts of racemic tamsulosin, like oxalate, salicylate, fumarate, tartrate, maleate and the like can be directly used in the resolution step without liberating the free base.

The resolution step is carried out by mixing suitable quantities of the salt of racemic tamsulosin and S(+)BPA in adequate amounts of an organic solvent or a mixture of organic solvent and water mixture. The temperature may be maintained at ambient to warm temperatures (about 20 to about 60° C.) for several hours. A salt crystallizes out which was shown to be R-tamsulosin-(S)-BPA salt with chiral purity of 96.88% (Chiral HPLC) with only 3.12% of the S-tamsulosin-(S)-BPA salt. After filtering off the solid, the mother liquor is reserved for recovering the S-tamsulosin and the chiral resolving agent. The R-tamsulosin-S-BPA salt is well characterized by recording IR, $^1$H-NMR, $^{31}$P-NMR, XRD spectroscopic data and DSC thermogram, besides the optical rotation.

Optically pure tamsulosin free base is liberated from the respective resolved tamsulosin BPA salt by using a base like ammonia. For example R-tamsulosin-S-BPA salt of 96.88% enantiomeric excess (ee) is treated with aqueous ammonia to yield R-tamsulosin free base, which is extracted with ethyl acetate and isolated by removing the solvent with 99.04% ee and 99.56% chemical purity. The purified R-tamsulosin base may be used as such or may be further converted to its hydrochloride or other pharmaceutically acceptable salts.

Analogous to the above resolution, the salt of racemic tamsulosin is treated with R-BPA and solid S-tamsulosin-R-BPA salt is recovered. The mother liquor contains the R-tamsulosin-R-BPA salt which can be used for recovering the R-tamsulosin and the resolving agent. The S-tamsulosin-R-BPA salt is also characterized suitably.

The mother liquors from both the above resolutions contain one of the isomers enriched. Therefore the mother liquors are first treated with a base, to liberate the free tamsulosin base (mixture of R and S isomers), which can be extracted into an organic solvent like ethyl acetate and recovered as a solid after distilling off the solvent. The resolving agent remains in the aqueous phase in a microfine suspension as salt and can be liberated by addition of a mineral acid and completely recovered. The mixture of R and S isomers of tamsulosin obtained earlier is further processed as in the initial resolution step by using the appropriate resolving agent, i.e., S-BPA to recover R-tamsulosin as a solid or R-BPA to recover S-tamsulosin as a solid.

For clarity the resolution operations are summarized in the following charts 3 and 4.

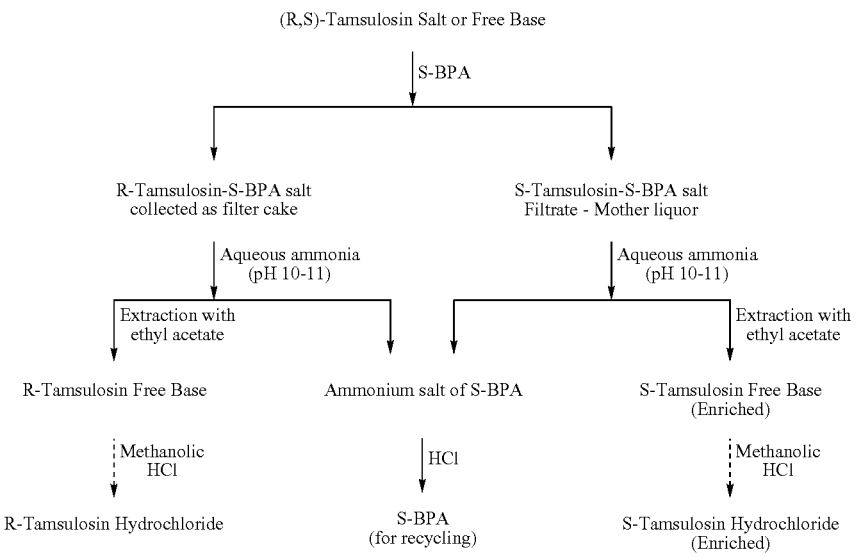

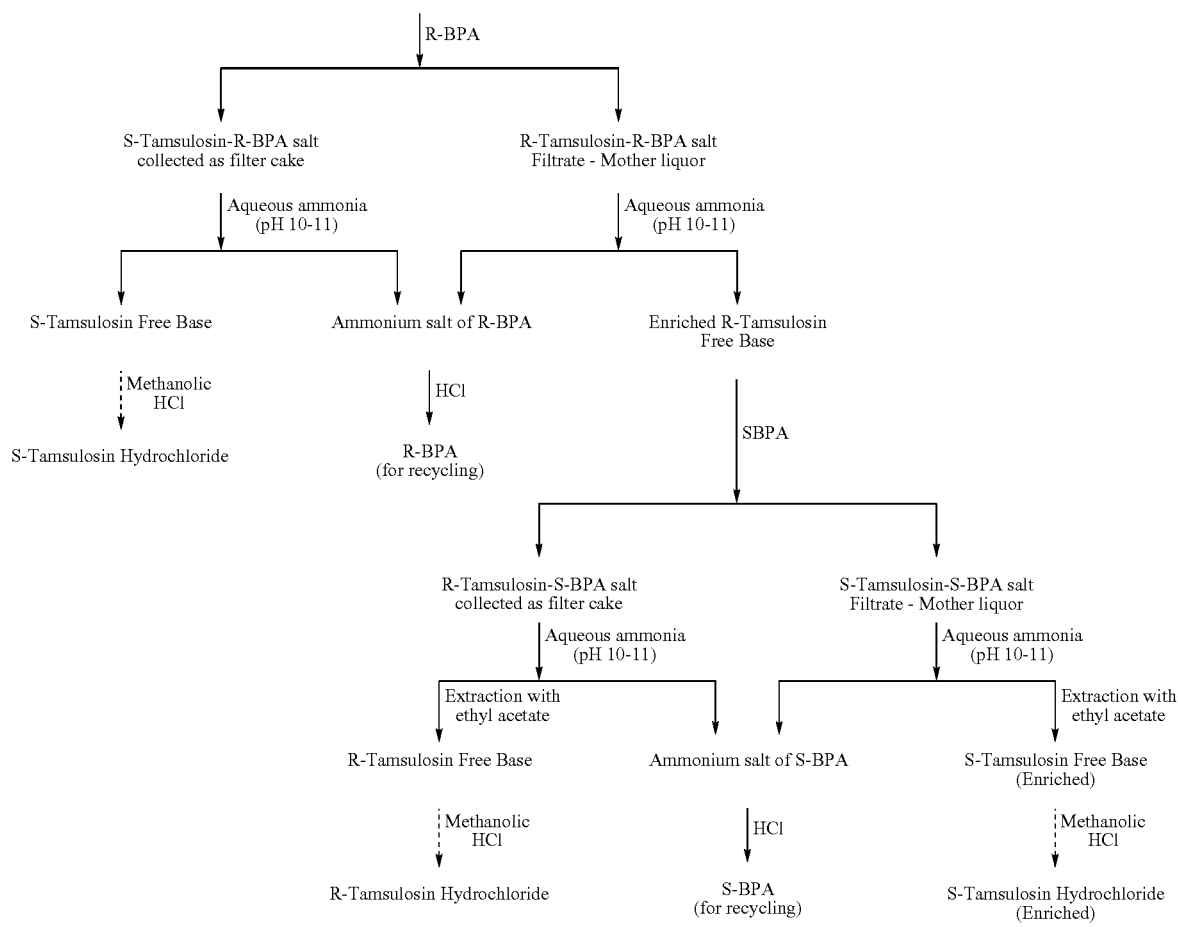

CHART 4 Resolution of (R,S)-Tamsulosin Salt or Free Base with R - BPA

EXAMPLES

The resolution steps described above and related operations and outcomes are illustrated with the Examples given below, without limiting the scope of the invention.

The racemic tamsulosin free base required for Examples 4 and 5 was prepared by modifying a process described in U.S. Pat. No. 4,703,063 and U.S. Pat. No. 4,731,478 (Examples 4 and 5 in both). For the sake of clarity and completeness this preparation is also described below.

Preparation of Racemic Tamsulosin Free Base a) 2-Methoxy-5-(2-oxopropyl)-benzene sulfonamide (37.3 gm, 153.3 mmol), 2-(2-ethoxyphenoxy)-1-ethanamine (29.8 gm, 164.4 mmol) and methanol (250 mL) were taken into a one liter stainless steel flask and mixed well. Catalyst Raney nickel (8 gm) was added to the flask and the mixture hydrogenated at 50° C. at hydrogen pressure of 40 psi for 30 hrs. The catalyst was removed by filtration and solvent from the filtrate was distilled off completely at 50° C. under vacuum. The dark brown crude obtained was treated with methanolic hydrochloric acid (175 mL) at 0-5° C. under stirring. Tamsulosin hydrochloride formed as a solid was filtered, washed with ethyl acetate (200 mL), suspended in methanol (120 mL) and the methanol slurry filtered to obtain off white solid material. It was dried for 3 hrs at 80° C. to give racemic tamsulosin hydrochloride. Melting point 255-257° C., chemical purity of 98.8 area % (by HPLC) and R,S ratio of 51.45:48.55 (by chiral HPLC).

b) Racemic tamsulosin hydrochloride (25 gm) obtained by the process described in step (a) above was suspended in water (50 mL). A 15% solution of ammonium hydroxide (25 mL) was added to the mixture and stirred for two hours at room temperature. The solid material was filtered, washed with water (25 mL) and dried at 60° C. for 3 hrs under vacuum (3 torr) to afford racemic tamsulosin free base (yield 22.3 gm, 97.1%) of melting point 127-130° C., chemical purity of 98.15% (area % by HPLC) and R,S ratio of 51.65:48.35, (by chiral HPLC).

Example 1

Synthesis of Salts of Racemic Tamsulosin (a) Synthesis of Oxalate Salt of Racemic Tamsulosin 2-(o-Ethoxyphenoxy)ethylamine (45 gm) was dissolved in methanol (250 mL). To this 2-methoxy-5-(2-oxopropyl)-benzene sulfonamide (55 gm), catalyst 5% platinum on carbon (12.1 gm) and methanol (330 mL) were added. The mixture was hydrogenated in autoclave at 55° C. at hydrogen pressure of 13 kg/cm² for 5 hrs. The reaction mixture was cooled and the catalyst was filtered off. To the filtrate containing racemic tamsulosin, oxalic acid (14.3 gm) was added and the solvent was distilled off. To the residue, acetone (700 mL) was added and stirred at reflux temperature for 30 mins. The mixture was cooled, filtered, and the filter cake washed with acetone (50 mL). The salt was further purified by suspending the material in 2-propanol at reflux temperature, cooling to ambient temperature and filtering the solid. The pure oxalate salt of racemic tamsulosin shows a melting range of: 178-182° C. and HPLC purity: 97.24 (area %). The chiral HPLC showed it to be a mixture R and S isomers in the ratio of 50.1 to 49.9. The infrared spectrum of the oxalate salt of racemic tamsulosin as shown in FIG. 1 of the drawing accompanying this specification, exhibited peaks at cm$^{-1}$: 1154 & 1332 ($SO_2$), 3408 (—$NH_2$), 2983 ($NH_2$+), 1591 (COO—). The $^1$H-NMR spectrum in $CD_3SOCD_3$ gave signals at δ values: 1.06-1.08 (3H, d, >CH—$CH_3$), 1.30-1.33 (3H, t, —$CH_2$—$CH_3$), 3.89 (3H, s, —$OCH_3$), 4.15-4.36 (10 H, 4-$CH_2$, —CH, —NH), 7.61 (2H, s, —$NH_2$), 6.8-7.5 (7H, m, Ar—H).

The $^{13}$C-NMR spectrum exhibited signals as expected, in particular at δ values: 56.34 (—$OCH_3$), 14.93 (—$OCH_2$$CH_3$), 17.29 (—$CH.CH_3$), 54.59 (—$CH.CH_3$), 64.11 (—O$CH_2.CH_3$), 44.51 (—NH.$CH_2.CH_2.CH_2$.O—), 67.25 (—NH.$CH_2.CH_2$.O—), 39.53 (—$CH_2$.CH—), 165.35 (COOH oxalate). Element analysis: C=53.64% (Calcd. 53.49%), H=6.57% (Calcd. 6.62%), N=5.89% (Calcd. 5.95%) and S=6.58% (Calcd. 6.79%) and corresponds to the hydrate, M.Wt. 471.53, $C_{21}H_{29}N_2O_7S.H_2O$.

Figure 2:
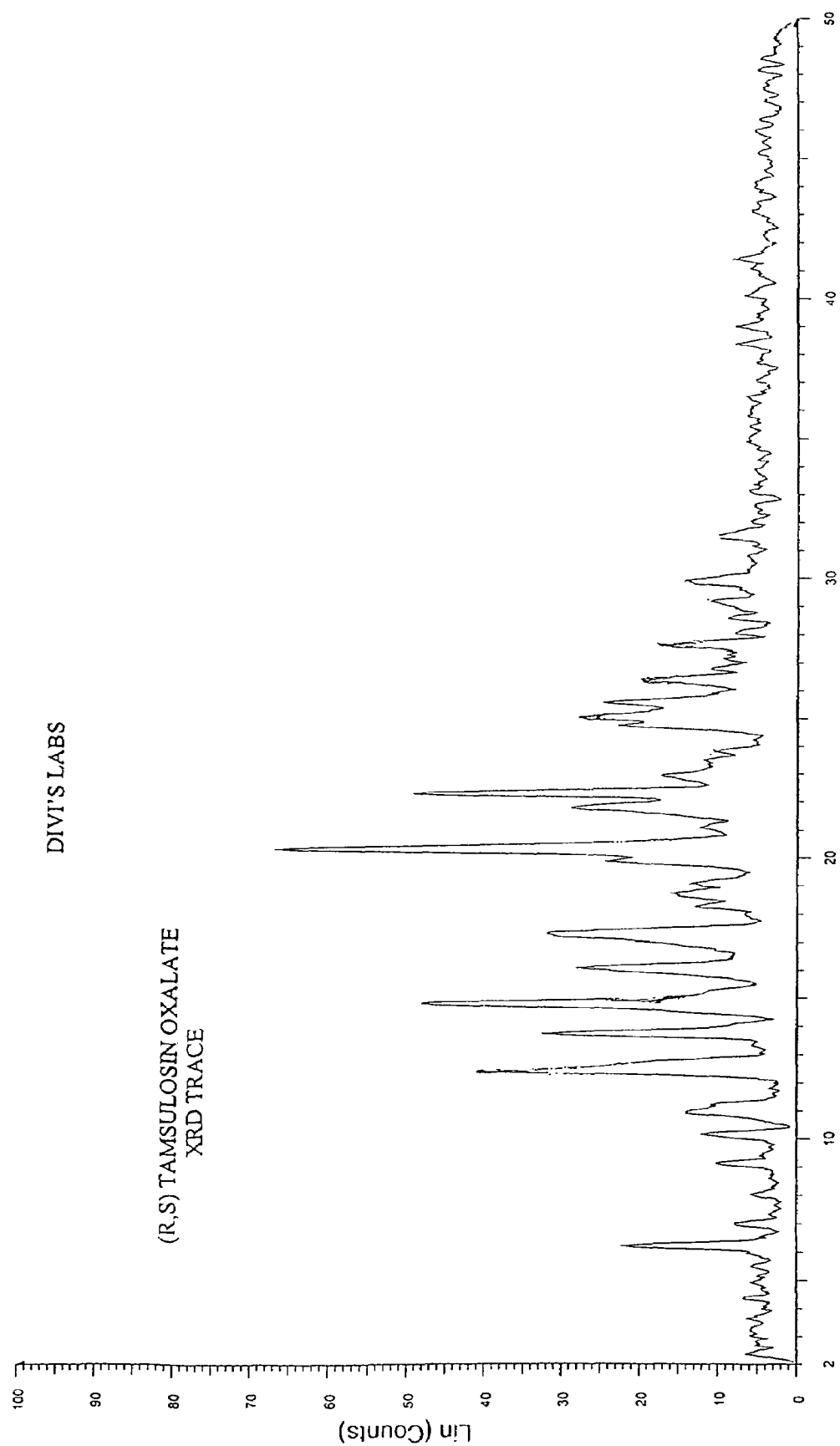
FIG. 2: (R,S)-Tamsulosin oxalate (XRD Trace).
Figure 3:
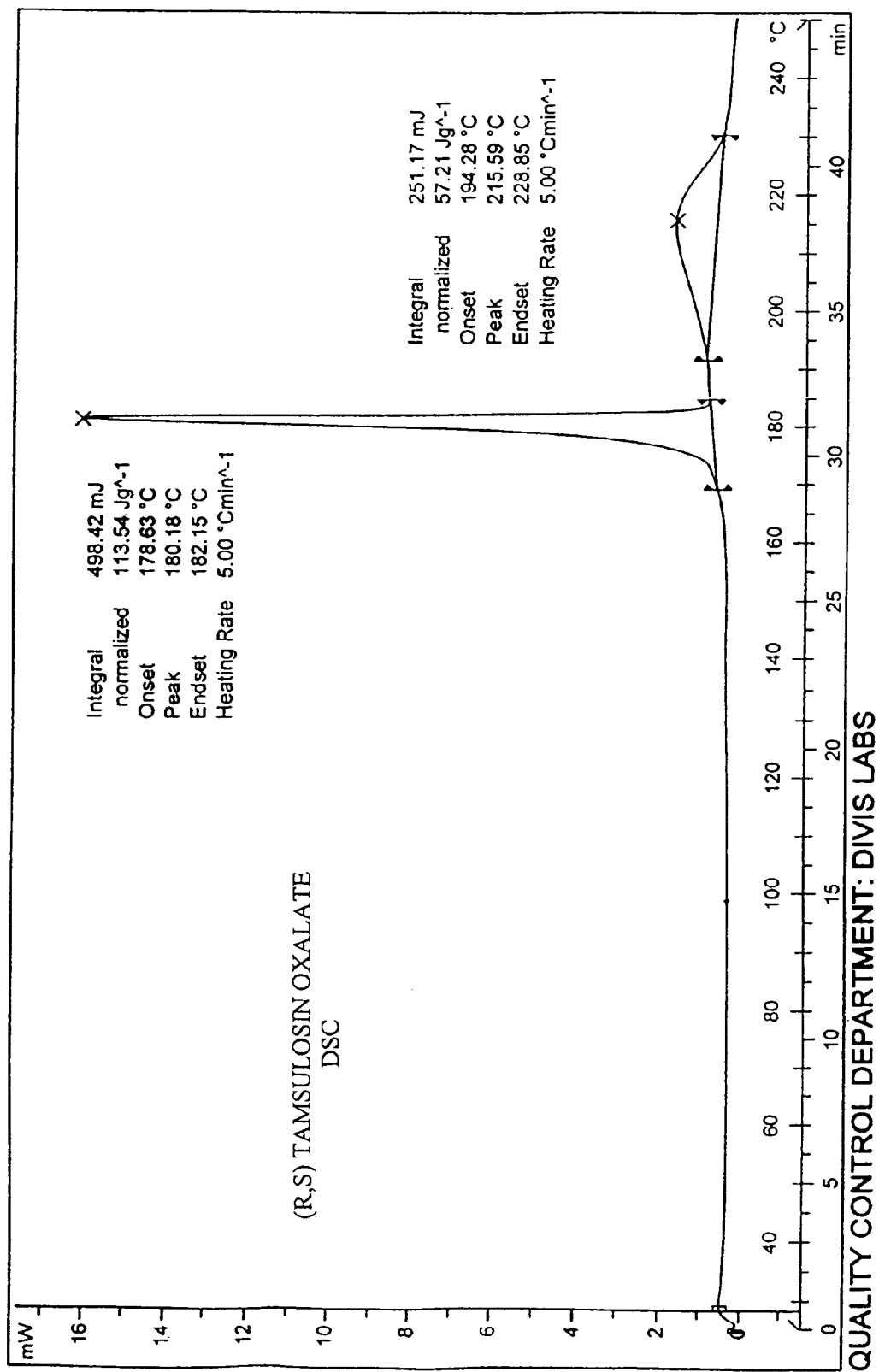
FIG. 3: (R,S)-Tamsulosin oxalate (DSC).

The ES-mass spectrum signal at m/z=409 corresponded to mass of free base. The XRD trace shows strong peaks at 2 theta values: 20.36, 22.33, 14.8, and 13.74 in that sequence as shown in FIG. 2. The DSC thermogram of pure salt exhibited a sharp peak at 180.2° C. as shown in FIG. 3.

These data confirm the structure of the oxalate salt of racemic tamsulosin.

(b) Preparation of Fumarate Salt of Tamsulosin

The fumarate salt of racemic tamsulosin was prepared in a similar manner as described in (a) above, by using 13.12 gm (0.2 eq) of fumaric acid in place of oxalic acid. The purified salt showed a melting range of 200-202° C. and a chemical purity (HPLC) of 98.89%.

(c) Preparation of Maleate Salt of Racemic Tamsulosin

The maleate salt of racemic tamsulosin was prepared in a similar manner as described in (a) above, by using 13.12 (0.5 gm) of maleic acid in place of oxalic acid and ethyl acetate in place of acetone. The purified salt showed a melting range of 155-159° C. and a chemical purity (HPLC) of 98.5%.

(d) Preparation of Salicylate Salt of Racemic Tamsulosin

The salicylate salt of racemic tamsulosin was prepared in a similar manner as described in (a) above, by using 32.48 gm (1.04 eq) of salicylic acid in place of oxalic acid and dichloromethane in place of acetone. The purified salt showed a melting range of 47-52° C. and a chemical purity (HPLC) of 98.41%.

(e) Preparation of Tartrate Salt of Racemic Tamsulosin

The tartrate salt of racemic tamsulosin was prepared in a similar manner as described in (a) above, by using 16.97 gm (0.5 eq) of (+) tartaric acid in place of oxalic acid and ethyl acetate in place of acetone. The purified salt showed a melting range of 197-199° C. and a chemical purity (HPLC) of 98.5%.

Example 2

Resolution of Oxalate Salt of Racemic Tamsulosin with (S)-(+)-1,1'-binaphthyl-2,2'-diyl Hydrogen Phosphate (S-BPA)

(a) Preparation of R-Tamsulosin-S-BPA Salt

Figure 4:
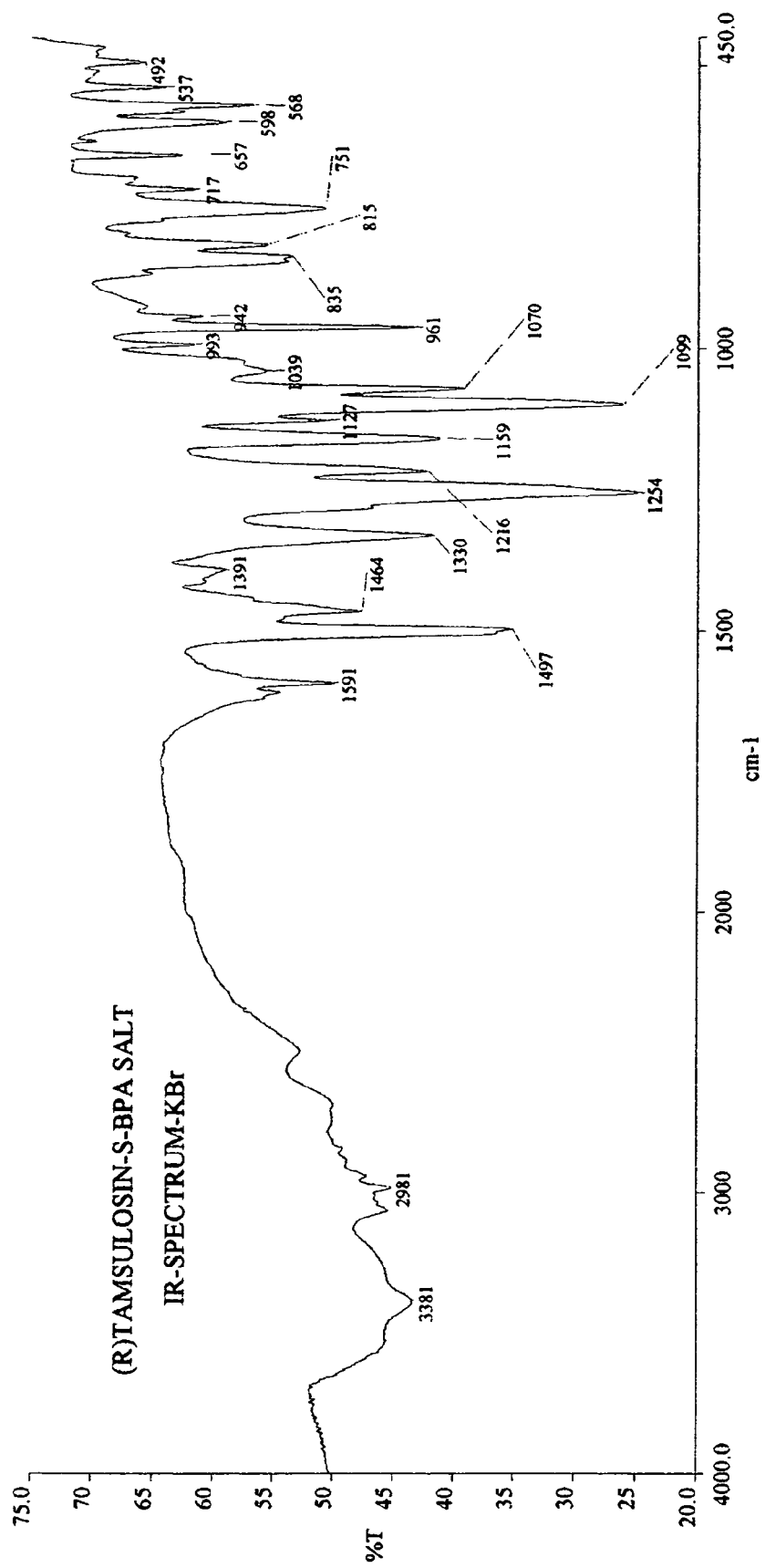
FIG. 4: (R)-Tamsulosin-S-BPA Salt (IR Spectrum-KBr).
Figure 5:
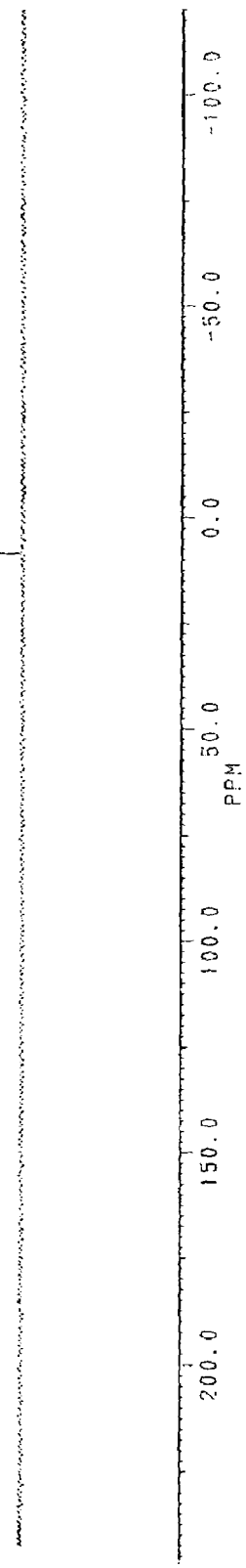
FIG. 5: (R)-Tamsulosin-S-BPA Salt ($^{31}$P-NMR).
Figure 6:
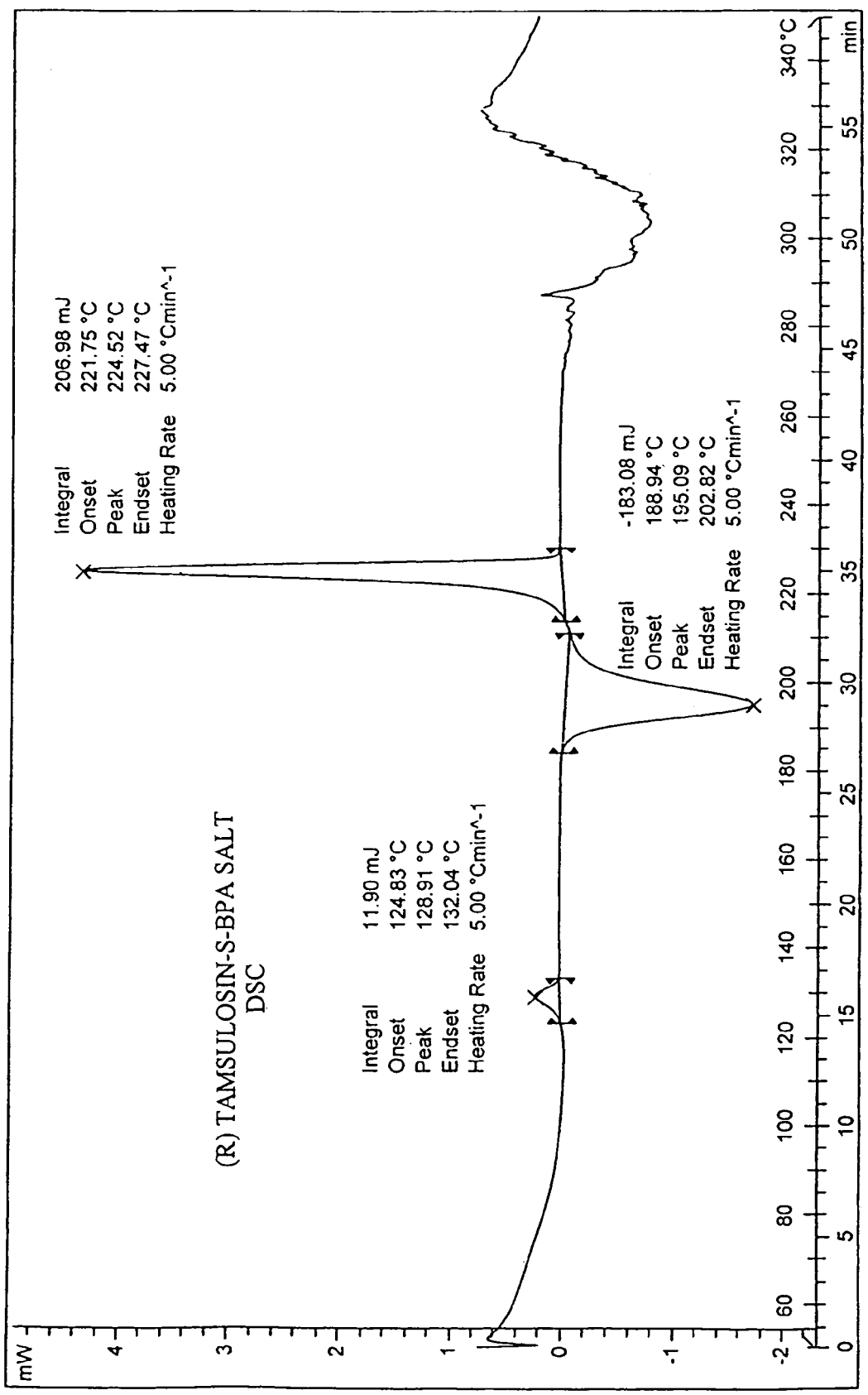
FIG. 6: (R)-Tamsulosin-S-BPA Salt (DSC).
Figure 7:
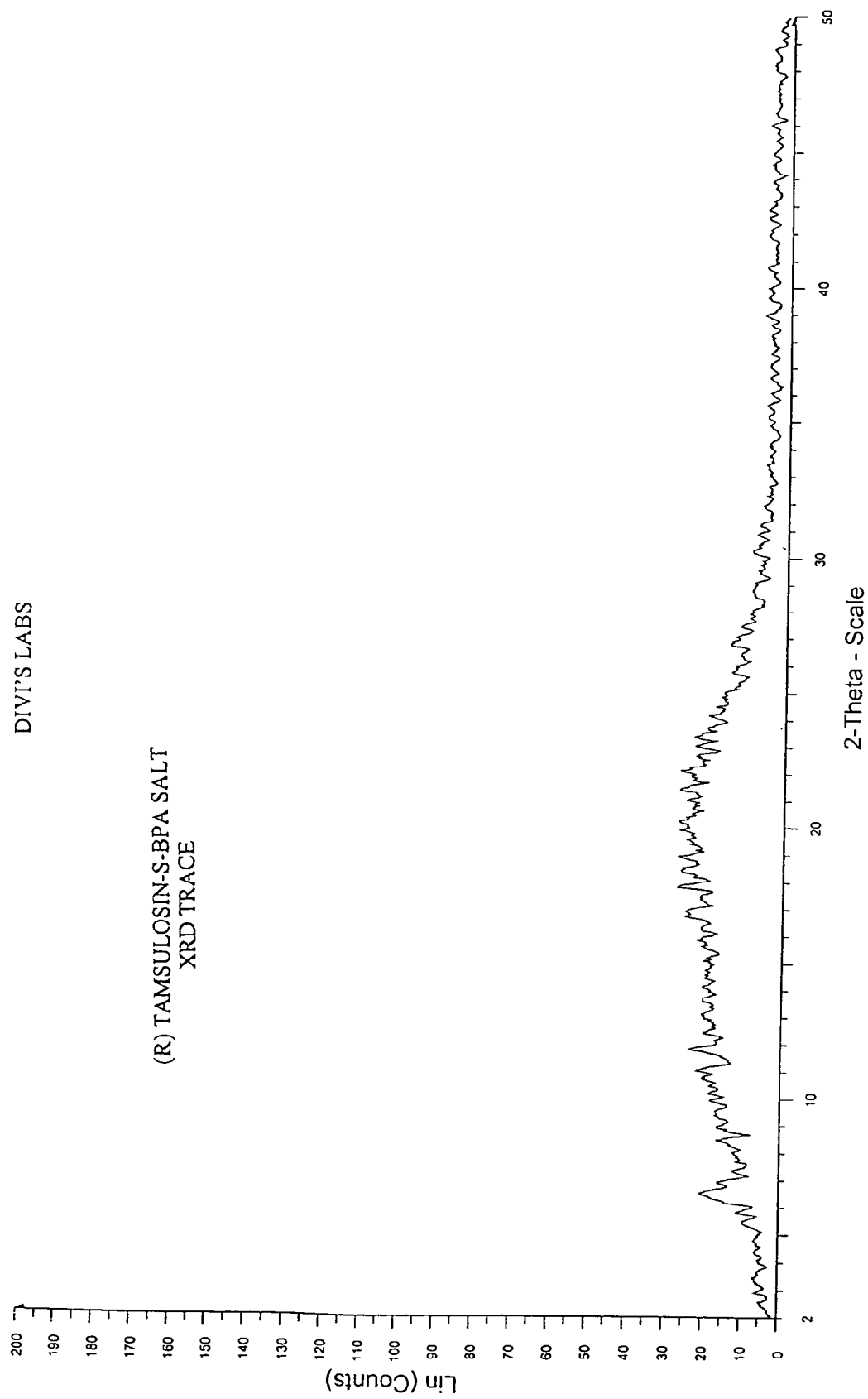
FIG. 7: (R)-Tamsulosin-S-BPA Salt (XRD Trace).

Racemic oxalate salt of tamsulosin (10 gm, 21.2 mmol) obtained by the process described in Example 1 and S-BPA (7.4 gm, 21.2 mmol) were taken in a mixture of acetone (331 mL) and water (15 mL). The mixture was stirred at 50-55° C. for 25 mins, cooled to 27-30° C. and stirred for 5 hrs. The R-tamsulosin-S-BPA salt formed was collected by filtration and washed with acetone (20 mL). The combined filtrate and washings were reserved for recovery of the S-isomer. (see step (d) below) It was dried at 80° C. for 2 hrs and then at 110° C. for 5 hrs to afford 5 gm of (R)-tamsulosin-(S)-BPA salt, exhibiting optical rotation, $[\alpha]^{24}D_=+268.33°$ (C=0.35, methanol) and a chiral purity of 96.88% R-isomer with 3.12% of S-isomer (chiral HPLC). The infrared spectrum substantially corresponds to the structure of the diastereomeric R-tamsulosin S-BPA salt as shown in FIG. 4. Its identity was proved by $^1$H-NMR, $^{13}$C-NMR and $^{31}$P-NMR spectra as shown in FIG. 5. For further characterization of the salt the differential scanning calorimetry (DSC) and X-ray diffractogram have been recorded as shown in FIGS. 6 & 7 respectively. The XRD trace indicates amorphous nature of the salt.

(b) Conversion of R-Tamsulosin-S-BPA Salt to R-Tamsulosin Free Base

Figure 8:
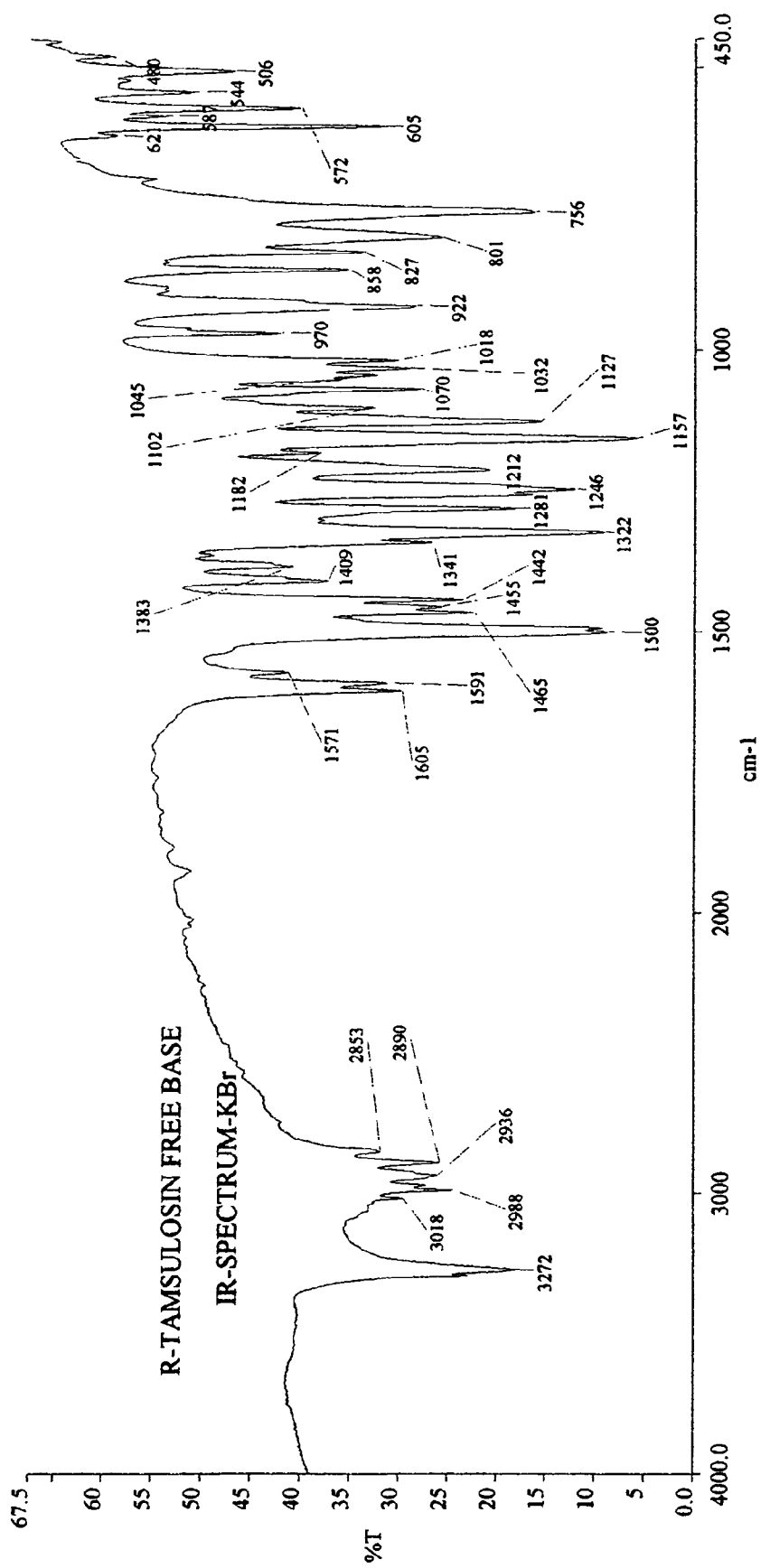
FIG. 8: (R)-Tamsulosin Free Base (IR Spectrum-KBr).
Figure 9:
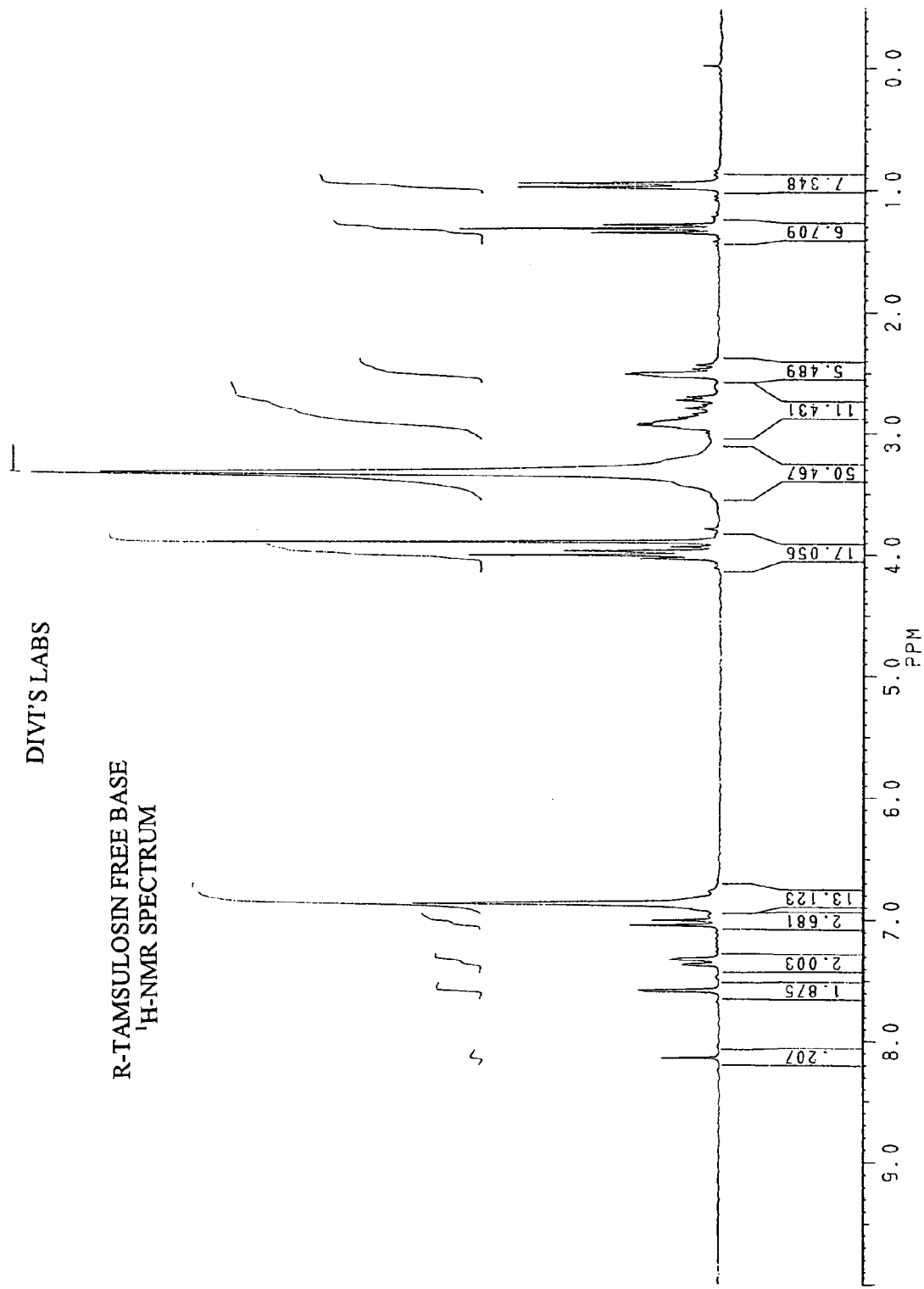
FIG. 9: (R)-Tamsulosin Free Base ($^1$H-NMR).
Figure 10:
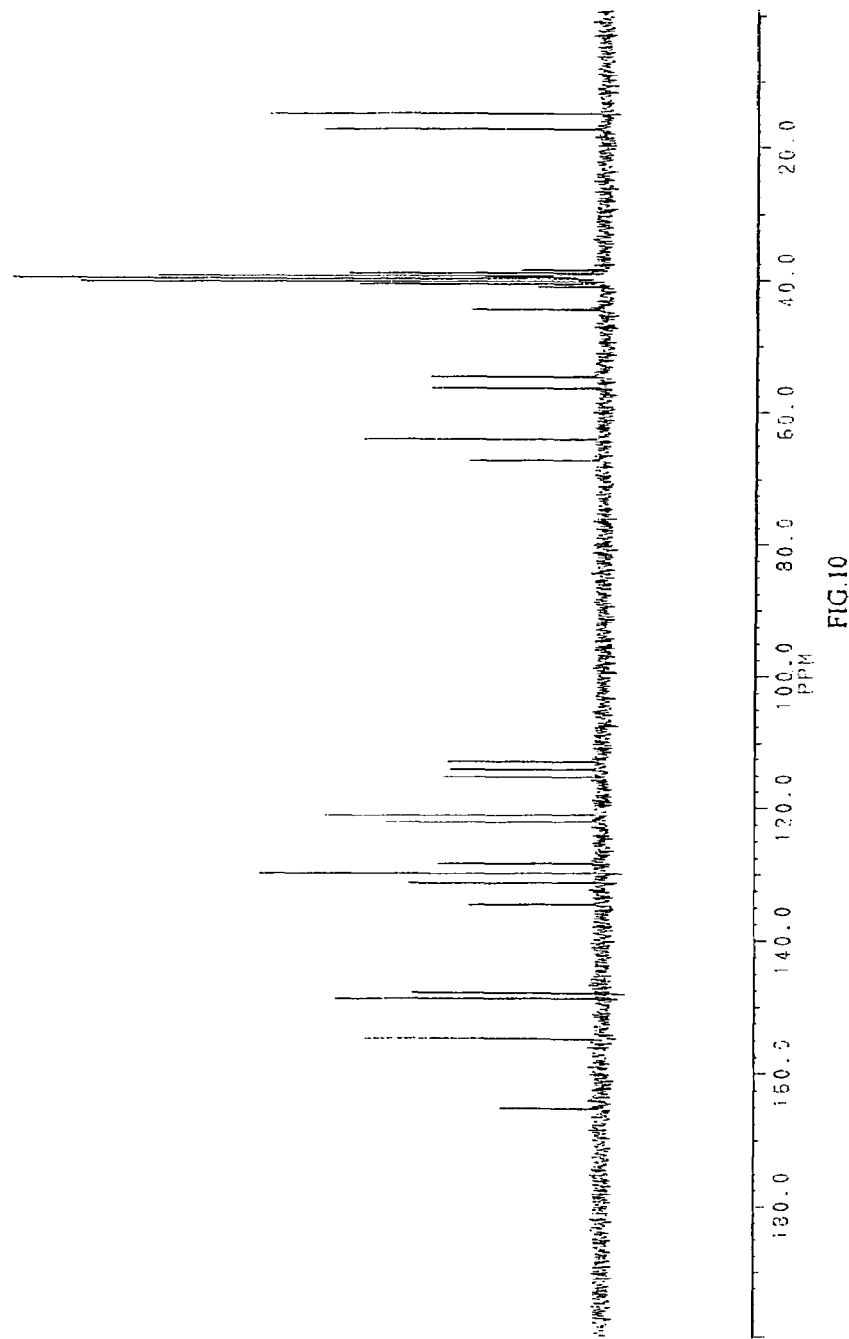
FIG. 10: (R)-Tamsulosin Free Base ($^{31}$C-NMR Spectrum).
Figure 11:
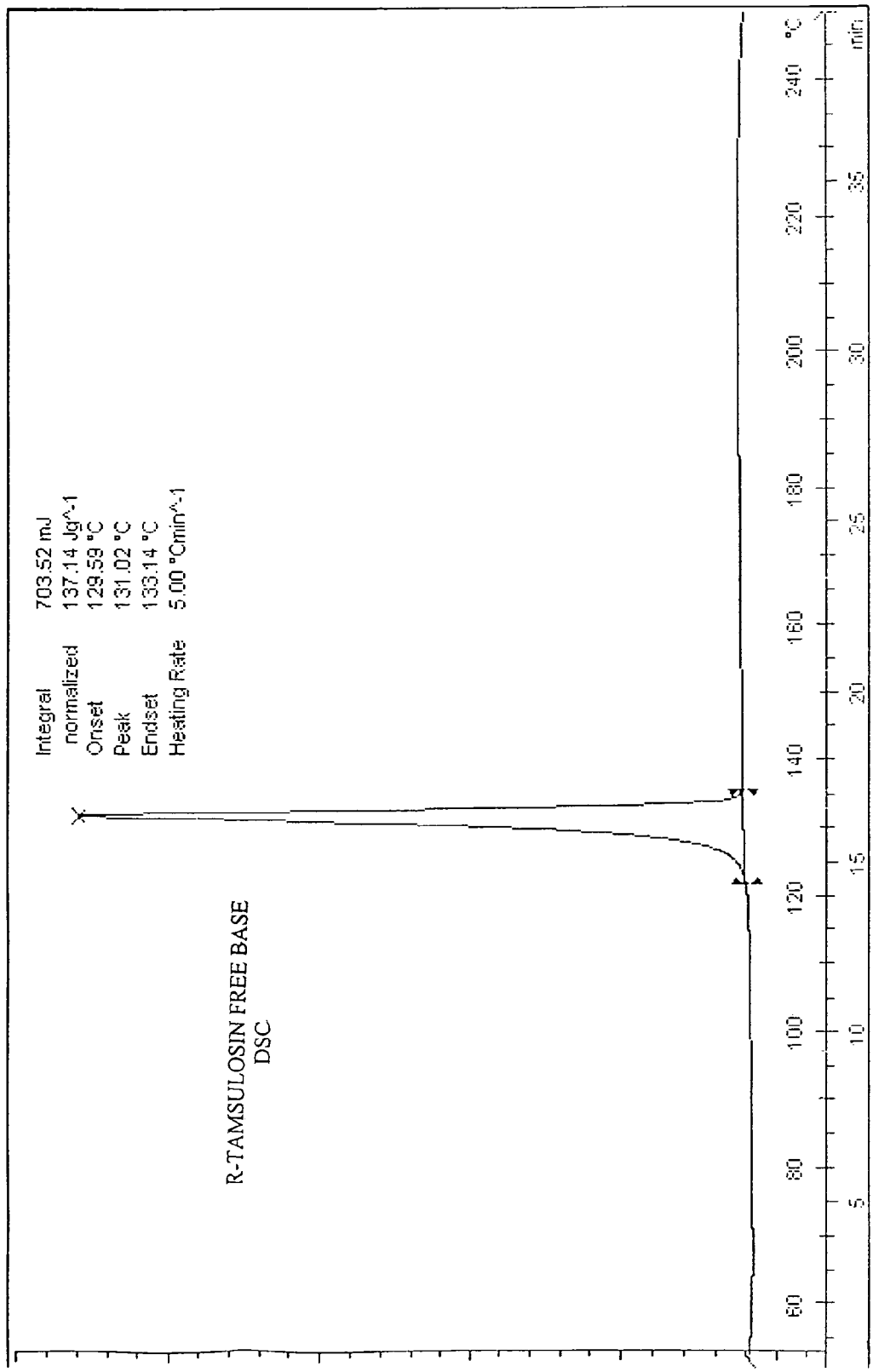
FIG. 11: (R)-Tamsulosin Free Base (DSC).
Figure 12:
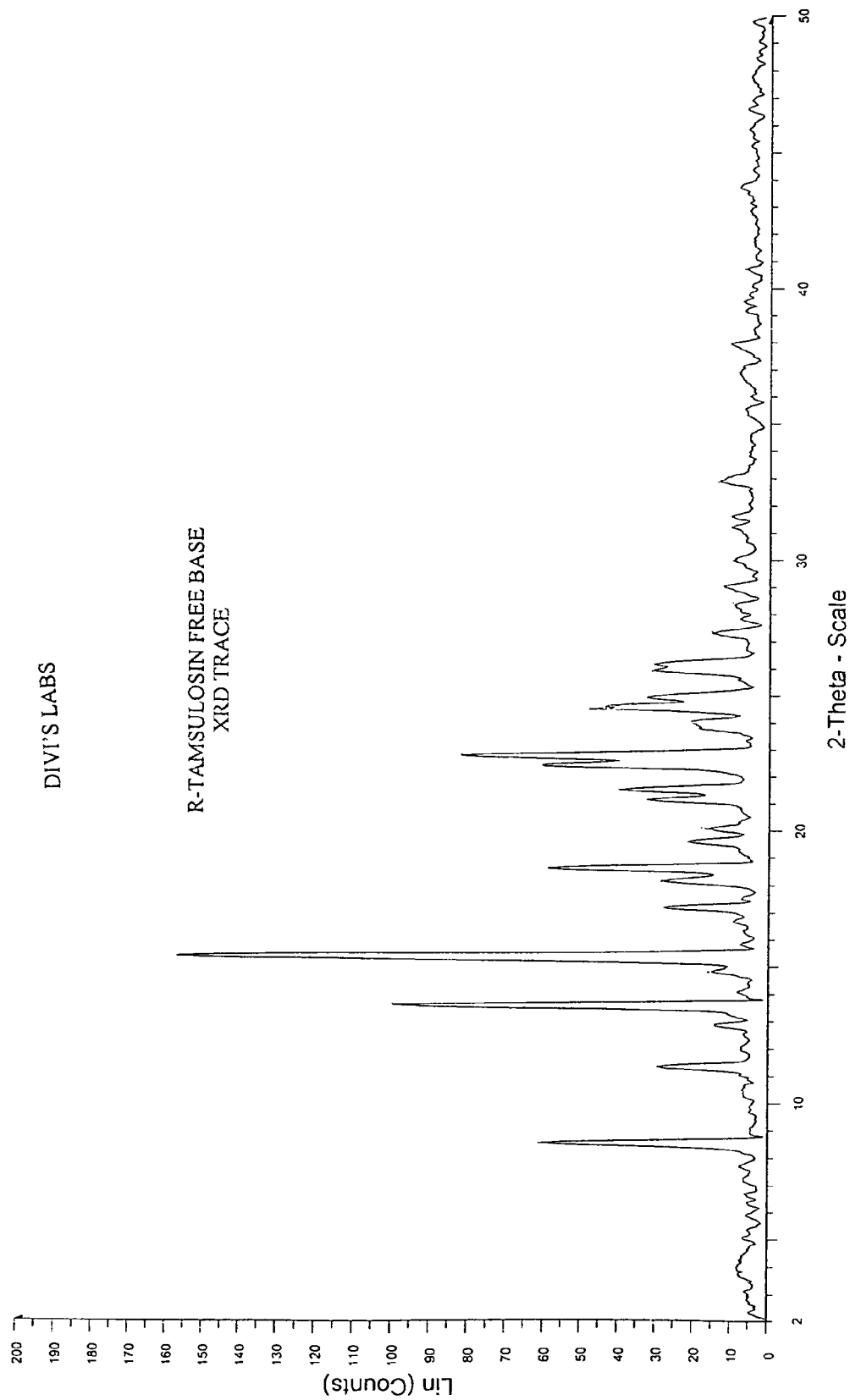
FIG. 12: (R)-Tamsulosin Free Base (XRD Trace).

R-Tamsulosin-S-BPA salt (5 gm) obtained by the process described in step (a) above was suspended in water (100 mL) and stirred for 10 mins at 25-30° C. The suspension was adjusted to pH of 10.5 with 15% aqueous ammonia solution and then stirred at 45-50° C. for 30 mins. After allowing the suspension to arrive at about ambient temperature it was extracted with ethyl acetate (6×100 mL). The aqueous phase and water washings were combined and reserved for recovery of S-BPA. The combined extracts were washed with water (3×100 mL) then with brine solution (2×100 mL) and dried over anhydrous sodium sulphate. The dried extract (organic layer) was filtered and concentrated in vacuum to give solid material, which after drying at 50° C. for 2 hrs yielded 2.45 gm (90.8%) of R-tamsulosin free base. It shows specific optical rotation of $[\alpha]^{24}D=-15.88°±1°$ (C=0.35, methanol), 99.04% ee of R-isomer by chiral HPLC and 99.56 area % chemical purity by HPLC. Pure R-isomer base obtained after conversion to hydrochloride salt and re-liberated by alkaline treatment shows m.p. 131-133° C. It was further characterized by elemental analysis: C=58.86% (Calcd. 58.80%), H=6.89% (Calcd. 6.91%), N=6.88% (Calcd. 6.86%) and S=7.79% (Calcd. 7.84%) for $C_{20}H_{28}N_2O_5S$ (Mol.wt: 408.5 1), infra-red spectrum as shown in FIG. 8, $^1$H-NMR and $^{13}$C-NMR spectra as shown in FIGS. 9 & 10, ES-Mass spectrum (M+peak at m/z 409), DSC (FIG. 11) and XRD as shown in FIG. 12 traces.

(c) Conversion of R-tamsulosin Free Base into (R)-tamsulosin Hydrochloride (R)-(−)-Tamsulosin free base (2.45 gm) obtained in step (b) above was added to 70 mL of methanol and heated to 45° C. under stirring. Then it was treated with methanolic hydrochloric acid. The acid solution was concentrated in vacuum and residue suspended in 30 mL acetone. The solid material was collected by filtration, washed with acetone and dried at 50° C. for one hour to afford 2.6 gm (97.4%) of tamsulosin hydrochloride comprising 98.76% ee of R-isomer by HPLC, optical rotation $[\alpha]^{24}_D=-4.32°$ (C=0.35, methanol).

On crystallization from methanol, a white crystalline solid of R-tamsulosin hydrochloride of 99.4% ee of R-isomer (by chiral HPLC), 99.94% (area %) chemical purity by HPLC, and melting point: 231-233° C. (DSC) was obtained. Its identity was established by $^1$H-NMR, ES-Mass and IR spectra. Its XRD trace exhibited intense peaks at 2 theta values 11.13°, 16.71° and 22.33° (in that sequence).

(d) Isolation of S-Tamsulosin Free Base

The filtrate set aside in step (a) above was freed from acetone in vacuum and the residue treated with water (100 mL). The pH of the mixture was adjusted to 10.5 with 15% aqueous ammonia solution, heated at 45-50° C. under stirring for 30 mins. After allowing the mixture to cool to ambient temperature, it was extracted with ethyl acetate (6×100 mL). The combined extracts were washed with water (3×100 mL). The aqueous layer and water washings were combined and reserved for recovery of S-BPA (see step (e) below). The organic phase was then washed with brine solution (2×100 mL) and dried over anhydrous sodium sulfate. The dried extract was filtered and concentrated in vacuum to yield an off white solid which after drying at 50° C. for 2 hrs afforded 4.9 gm of tamsulosin free base of 66.9% ee of S-isomer (by chiral HPLC) and of 92.87% chemical purity (by HPLC, area %), melting range: 118-124° C., optical rotation: $[\alpha]^{24}_D = +12.42°\pm1°$ (C=0.35, methanol).

(e) Recovery of S-BPA from S-Tamsulosin S-BPA Salt

The aqueous layer reserved in step (d) was taken and its pH adjusted to 2 with hydrochloric acid (100 mL). The mixture was stirred for 2 hrs at ambient temperature. Material formed was filtered and washed with water (75 mL). The off white material collected was dried at 60° C., to afford to 4.2 gm of S-BPA of optical rotation $[\alpha]^{20}_D = +516.12°$ (C=1.35 methanol), melting point: >300° C.

In a similar manner fumarate, maleate, salicylate and tartrate salts of racemic tamsulosin could be resolved using S-BPA as resolving agent, to obtain R-tamsulosin free base.

Example 3

Figure 13:
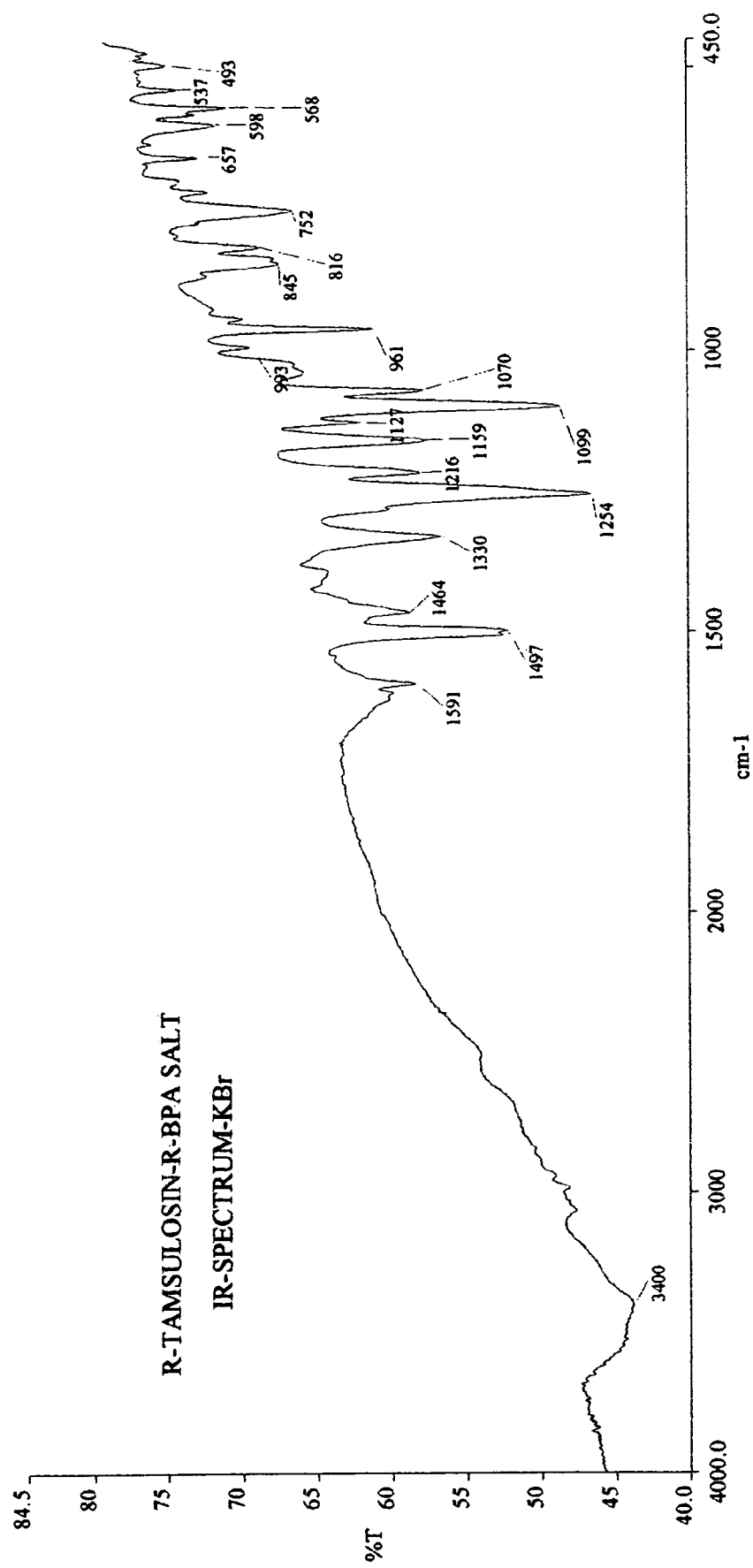
FIG. 13: (S)-Tamsulosin-R-BPA Salt (IR Spectrum-KBr).
Figure 14:
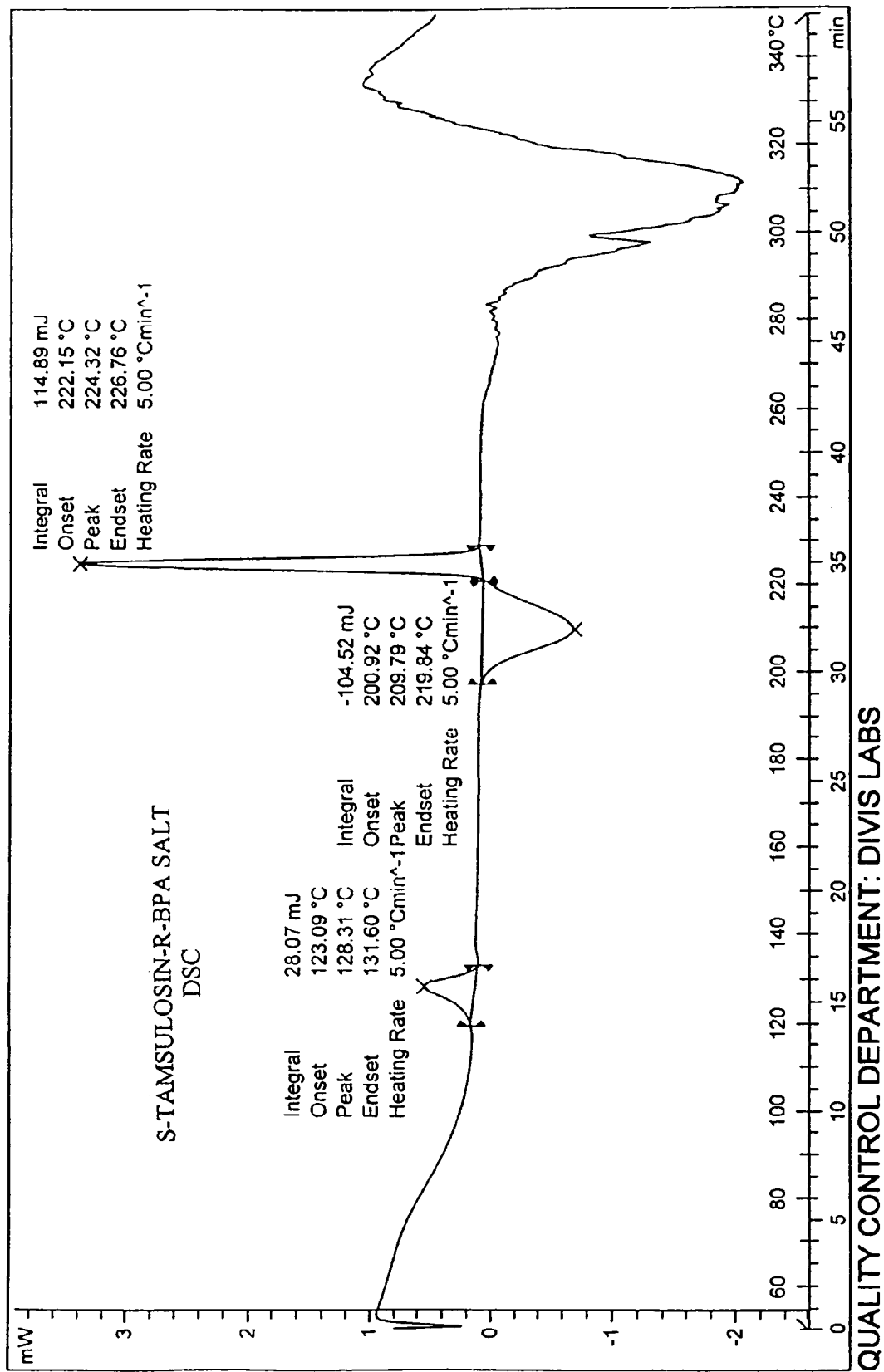
FIG. 14: (S)-Tamsulosin-R-BPA Salt (DSC).
Figure 15:
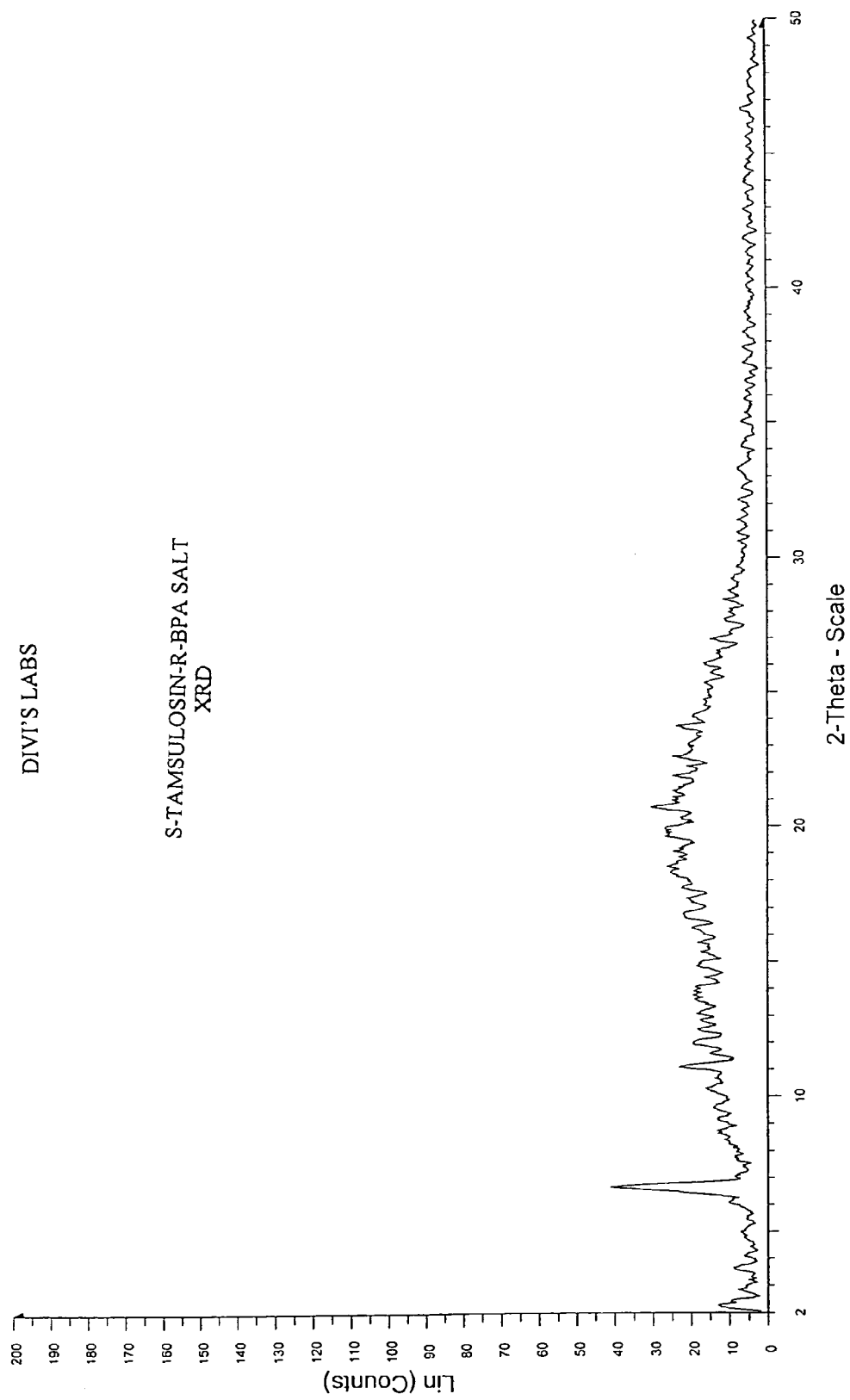
FIG. 15: (S)-Tamsulosin-R-BPA Salt (XRD Trace).

Resolution of Oxalate Salt of Racemic Tamsulosin with R-BPA (a) Preparation of S-Tamsulosin-R-BPA Salt Racemic oxalate salt of tamsulosin (3.0 gm, 6.36 mmol) obtained by the process described in Example 1 and R-BPA (2.21 gm, 6.35 mmol) were taken in a mixture of acetone (110 mL) and water (5.8 mL). The mixture was stirred at 50-55° C. for 25 minutes then cooled to 27-30° C. and stirred for 5 hrs. The formed salt was collected by filtration and washed with acetone (10 mL). The filtrate and washings were combined and reserved for recovery of R-tamsulosin. (see step (d) below) The salt was dried at 80° C. for 2 hrs and then at 110° C. for 5 hrs to afford 1.5 gm (31%) of S-tamsulosin-R-BPA salt of optical rotation $[\alpha C]^{24}_D = -270.16°$ (C=0.35, methanol). The salt was characterized by study of infrared spectrum as shown in FIG. 13 and $^1$H-NMR, $^{13}$C-NMR and $^{31}$P-NMR spectra as also by DSC as shown in FIG. 14 and XRD as shown in FIG. 15 traces.

(b) Conversion of S-Tamsulosin-R-BPA Salt to S-Tamsulosin Free Base

Figure 16:
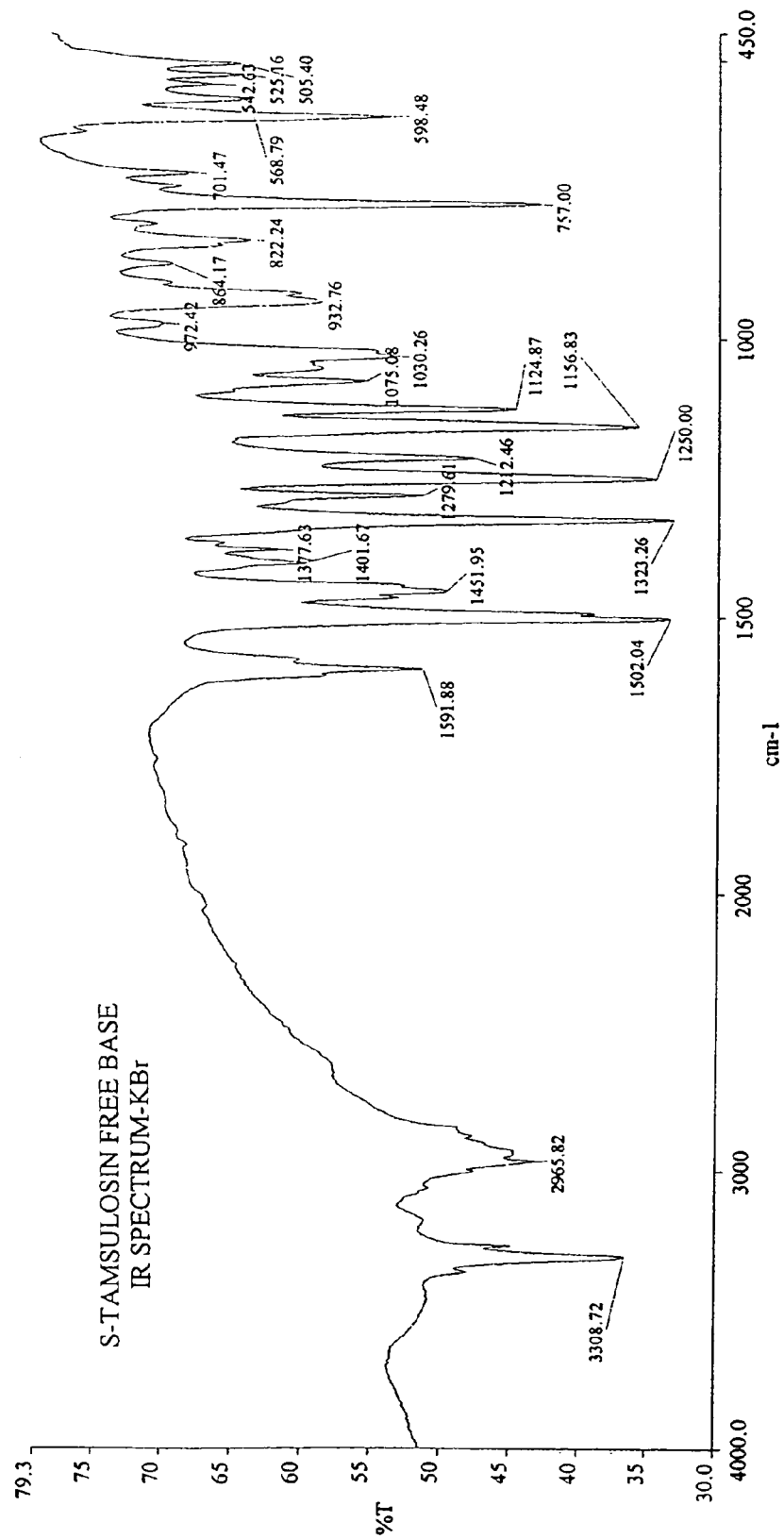
FIG. 16: (S)-Tamsulosin Free Base (IR Spectrum-KBr).
Figure 17:
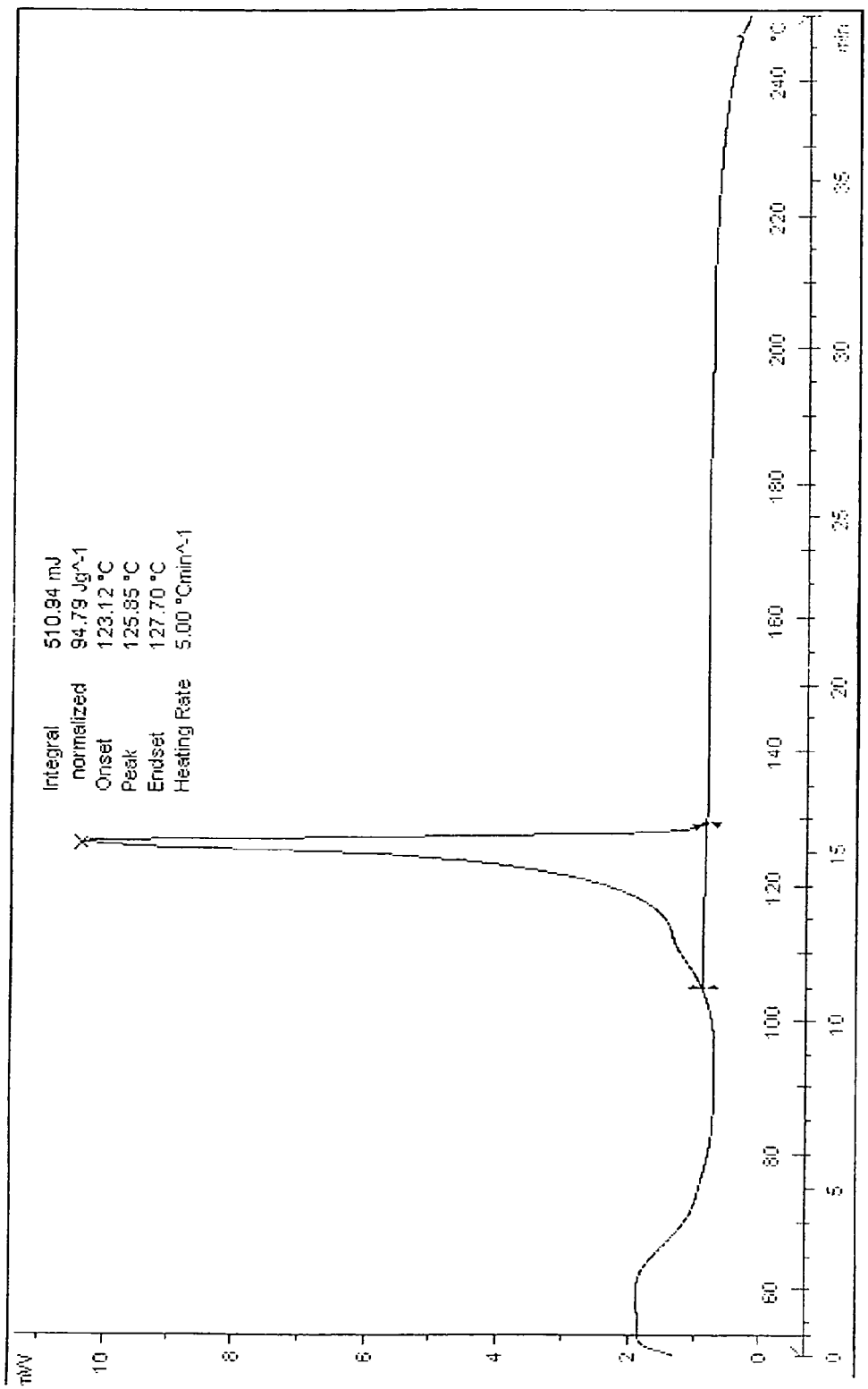
FIG. 17: (S)-Tamsulosin Free Base (DSC).
Figure 18:
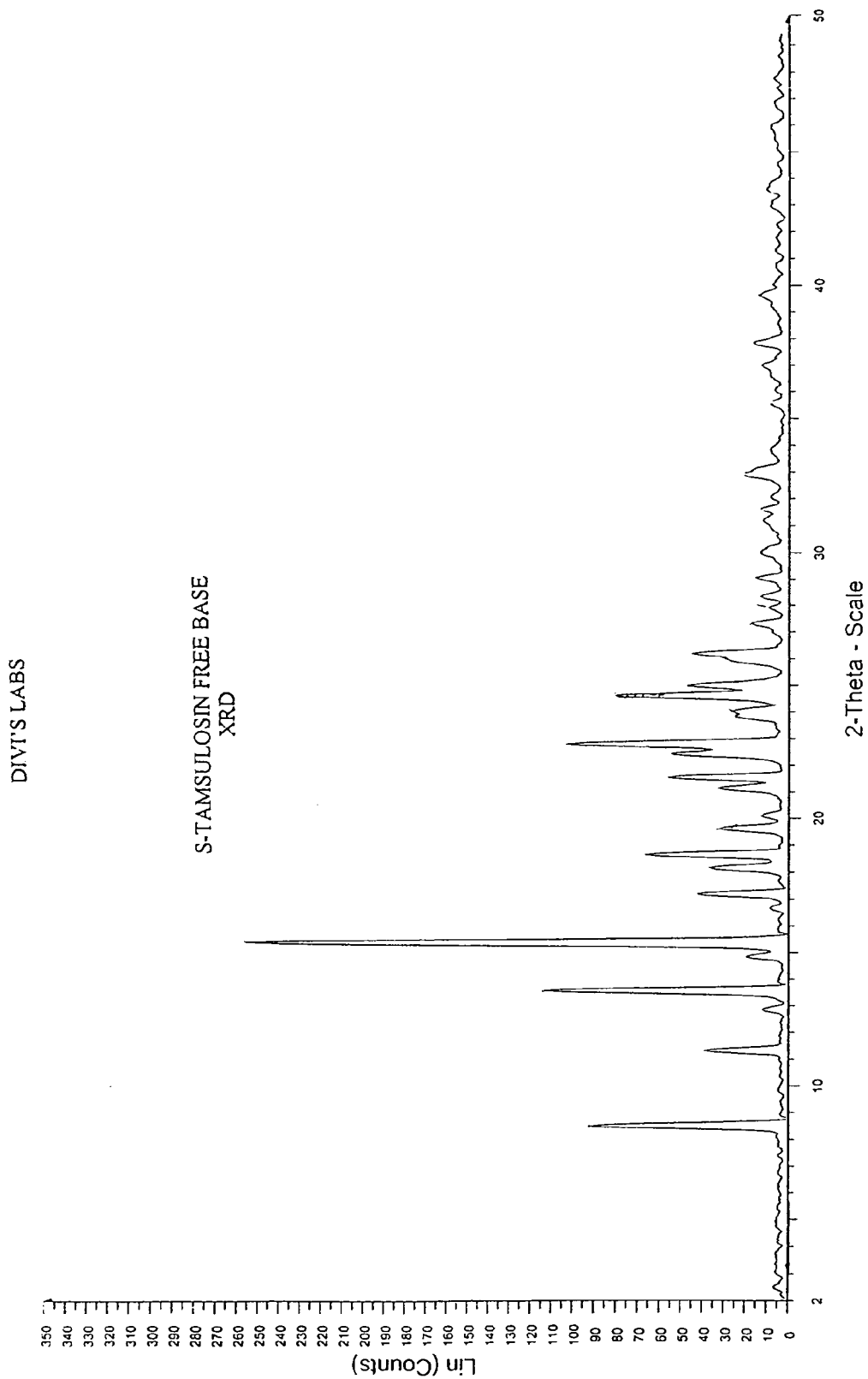
FIG. 18: (S)-Tamsulosin Free Base (XRD Trace).

S-Tamsulosin-R-BPA salt (1 gm) obtained in step (a) above was suspended in water (20 mL) and stirred for 10 mins at 25-30° C. The suspension was adjusted to pH 10.5 with 15% aqueous ammonia solution and then stirred at 45-50° C. for 30 mins. After allowing the suspension to ambient temperature it was extracted with ethyl acetate (6×20 mL). The extracts were washed with water (3×20 mL), then brine solution (2×20 mL). The organic solvent extracts were combined, dried over anhydrous sodium sulphate, filtered, concentrated in vacuum and the residue dried at 50° C. for 2 hrs to afford to 0.49 gm (90.8%) of S-tamsulosin free base of 99.06% ee of S-isomer by chiral HPLC and m.p. 122-126° C. Pure S-isomer base obtained after conversion to hydrochloride and reliberation by alkaline treatment shows m.p. 126-128° C. and specific optical rotation $[\alpha]^{24}_D = 13.77\pm1°$ (c=0.35 in MeOH). The S-tamsulosin free base was further characterized by its infrared spectrum as shown in FIG. 16, $^1$H-NMR, $^{13}$C-NMR and ES-mass spectra as also by DSC as shown in FIG. 17 and XRD as shown in FIG. 18 traces.

(c) Conversion of S-Tamsulosin Free Base to S-Tamsulosin Hydrochloride

Tamsulosin free base (0.385 gm) obtained in step (b) above was taken into methanol (11 mL), heated to 45° C. under stirring and treated with methanolic hydrochloride. The solution was concentrated in vacuum, the residue suspended in acetone (20 mL), filtered, washed with acetone and dried at 50° C. for one hour to afford 0.325 gm (77.5%) of S-tamsulosin hydrochloride of 99.03% ee of S-isomer by chiral HPLC. After recrystallization from methanol S-tamsulosin hydrochloride of 99.54% ee could be obtained. Melting point: 228-230° C. The IR absorbance spectrum is shown in FIG. 19.

(d) Recovery of R-Tamsulosin Free Base

The filtrate set aside in step (a) was freed from acetone in vacuum and the residue was treated with water (60 mL). The mixture was adjusted to pH 10.5 with 15% aqueous ammonia solution, and heated at 45-50° C. under stirring for 30 mins. After allowing the mixture to ambient temperature, it was extracted with ethyl acetate (6×50 mL). The combined extracts were washed with water (3×50 mL), then with brine solution (2×50 mL). The filtrate and aqueous washings were combined and reserved for recovery of S-tamsulosin free base (see below). The organic layer was dried over anhydrous sodium sulfate, filtered and concentrated in vacuum. The residual off white solid material was dried at 50° C. for 2 hrs to afford 1.3 gm of enriched tamsulosin free base of 57.8% ee of R-isomer (by chiral HPLC).

Tamsulosin free base (0.5 gm) containing 57.8% of R-isomer obtained as above was treated with same equivalent of S-BPA in acetone-water mixture and stirred for about 30 mins and cooled. The R-tamsulosin-S-BPA salt formed was collected by filtration and washed with acetone affording 0.35 gm (38%) of R-tamsulosin-S-BPA salt of optical rotation $[\alpha]^{24}_D = +267.3°$ (C=0.35, methanol). Then it was suspended in water, treated with 15% aqueous ammonia to decompose the salt. The freed tamsulosin base was extracted with ethyl acetate, the extract washed with brine, dried over anhydrous sodium sulfate, filtered and concentrated to yield R-tamsulosin free base. The aqueous phases contain ammonium salts of S-BPA, suitable for recovery of S-BPA and recycling.

Recovery of S-Tamsulosin Free Base

The aqueous phase reserved in (d) above contains S-tamsulosin-S-BPA salt. It was treated with 15% ammonia solution to adjust the pH to about 10.5 and stirred for 30 mins at about 45° C. The mixture was cooled and extracted with ethyl acetate, the ethyl acetate extract was dried over anhydrous sodium sulfate, filtered and concentrated to recover S-tamsulosin free base.

Example 4

Resolution of Racemic Tamsulosin Free Base with S-BPA (a) Preparation of R-Tamsulosin-S-BPA Salt Racemic tamsulosin free base (5 gm, 12.2 mmol) and S-BPA (4.24 gm, 12.2 mmol) were taken in a mixture of acetone (194 mL) and water (6.3 mL). The mixture was stirred at 50-55° C. for 25 mins and the clear solution stirred at 25-30° C. overnight. The formed salt was collected by filtration and washed with acetone (20 mL). The combined filtrate and washings was reserved for recovery of S-tamsulosin free base. (see step (c) below) The salt was dried at 80° C. for 2 hrs and then at 110° C. for 5 hrs to afford 3.9 gm (42.1%) of R-tamsulosin-S-BPA salt with an optical rotation of $[\alpha]^{24}_D=+267.5°$ (C=0.35, methanol).

(b) Conversion of R-Tamsulosin-S-BPA Salt to R-Tamsulosin Free Base

R-Tamsulosin-S-BPA salt (3 gm) obtained in step (a) above was suspended in water 77 mL and stirred for 10 mins at 25-30° C. The suspension was adjusted to pH 10.5 with 15% aqueous ammonia solution and then stirred at 50° C. for 30 mins. After allowing the suspension to ambient temperature it was extracted with ethyl acetate (5×77 mL). The extracts were combined and washed with water (3×77 mL). The aqueous phase and washings were combined and reserved (See (c) below) for recovery of S-tamsulosin free base. The organic phase was washed with brine solution (2×77 mL), dried over anhydrous sodium sulfate, filtered and concentrated in vacuum. The solid residue was dried at 50° C. for 2 hrs to afford 1.4 gm (86%) of R-tamsulosin free base of 98.35% ee of R-isomer. Melting point: 118-120° C., chemical purity 99.24 area %.

(c) Recovery of S-Tamsulosin Free Base

The filtrate set aside in steps (a) & (b) above, was freed from remaining acetone in vacuum. The residue was adjusted to a pH of 10.5 with 15% aqueous ammonia solution and heated at 45-50° C. under stirring for 30 mins. After allowing the mixture to ambient temperature, it was extracted with ethyl acetate (5×100 mL). The combined extracts were washed with water (3×100 mL) and then with brine solution (2×100 mL). The organic layer was separated, dried over anhydrous sodium sulphate. The dried extract was filtered and concentrated in vacuum to give solid material. The off white solid material was collected and dried at 50° C. for 2 hrs to afford 2.2 gm of tamsulosin free base containing 84.12% ee of S-isomer by chiral HPLC (FIG. 23) and chemical purity by HPLC of 98.17 area % (FIG. 24). Melting range: 120-124° C.

Example 5

Resolution of Racemic Tamsulosin Free Base with R-BPA (a) Preparation of S-Tamsulosin-R-BPA Salt Racemic tamsulosin free base (5 gm, 12.2 mmol) and R-BPA (4.24 gm, 12.2 mmol) were taken in a mixture of acetone (194 mL) and water (6.3 mL). The mixture was stirred at 50-55° C. for 25 mins and the clear solution stirred at 25-30° C. overnight. The formed salt was collected by filtration, washed with acetone (20 mL) and dried at 80° C. for 2 hrs and then at 110° C. for 5 hrs to afford 3.8 gm (41%) of S-tamsulosin-R-BPA salt of optical rotation $[\alpha]^{24}_D$: −265.9° C. (C=0.35, methanol).

(b) Conversion of S-Tamsulosin-R-BPA Salt to S-Tamsulosin Free Base

S-Tamsulosin-R-BPA salt (3 gm) obtained in step (a) above was suspended in water (77 mL) and stirred for 10 mins at 25-30° C. The suspension was adjusted to pH 10.5 with 15% aqueous ammonia solution and then stirred at 50° C. for 30 mins. After allowing the suspension to ambient temperature, it was extracted with ethyl acetate (5×77 mL). The combined extract was washed with water (3×77 mL) and then with brine solution (2×77 mL). The organic solvent extract was dried over anhydrous sodium sulphate, filtered and concentrated in vacuum. The residue was dried at 50° C. for 2 hrs to afford 1.35 gm (83.4%) of S-tamsulosin free base of 98.1% ee of S-isomer.

(c) Conversion of S-Tamsulosin Free Base to S-Tamsulosin Hydrochloride

S-Tamsulosin free base (1.35 gm) obtained in step (b) above was taken into methanol (52 mL) and treated with methanolic hydrochloric acid under stirring. The solution was concentrated in vacuum and residue suspended in acetone (19 mL). The solid material was collected by filtration, washed with acetone and dried at 50° C. for one hour to afford 1.32 gm (89.8%) of S-tamsulosin hydrochloride of ee 99.03% and chemical purity of 99.54%. The melting point was measured to be 229-231° C.

Example 6

Conversion of R-Tamsulosin Free Base to R-Tamsulosin Salts (a) R-Tamsulosin Oxalate Salt (R)-Tamsulosin free base (11 gm, 26.93 mmol) and acetone (85 mL) were taken and stirred at reflux temperature for 15 mins. In an another flask oxalic acid (1.68 gm, 13.33 mmol) and acetone (20 mL) were taken and stirred at reflux temperature to get clear solution. The oxalic acid solution was added slowly to the tamsulosin solution, stirred the mixture at reflux temperature for 20 mins, cooled slowly to room temperature and continued for 30 mins. The precipitate formed was filtered under vacuum and washed with acetone (20 mL). Off white solid material was collected and dried in hot air oven at 60° C. for 3 hrs to afford 11.3 gm of (R)-tamsulosin oxalate salt with melting range 180-183.5° C., chemical purity by HPLC: 99.98% and 100% of (R)-tamsulosin oxalate salt (chiral HPLC). DSC: 178.8-180.3° (peak split); XRD: 20.3, 21.7, 23.0, 15.6, 18.5, 12.4, 26.4, 17.9, 12.7 & 16.5 (2 theta values in decreasing order of intensity).

(b) R-Tamsulosin Fumarate Salt (R)-Tamsulosin free base (13 gm, 31.82 mmol) and acetone (371 mL) were taken and stirred at reflux temperature to get clear solution. Fumaric acid (1.85 gm, 15.94 mmol) was dissolved in acetone (520 mL) at reflux temperature, and added slowly into the solution of tamsulosin at 40-45° C. The mixture was stirred at reflux temperature for 20 mins, cooled to room temperature and stirred for 2 hrs. The precipitate formed was filtered under vacuum, washed with acetone (20 mL), the off white material collected, and dried in hot air oven for 3 hrs to afford 13.3 gm of (R) tamsulosin fumarate salt. Melting range 191.6-194.2° C., chemical purity by HPLC: 96.24% and 100% of (R)-tamsulosin fumarate salt (chiral HPLC). DSC: 192.5° (sharp); XRD: 22.4, 15.3, 25.8, 19.1, 20.7, 10.3, 22.8, 11.5, 21.0, 12.3 (2 theta values in decreasing order of intensity).

(c) R-Tamsulosin Maleate Salt (R)-Tamsulosin free base (12 gm, 29.383 mmol) was dissolved in ethyl acetate (514 mL) at reflux temperature. Maleic acid (1.7 gm, 14.65 mmol) was dissolved in ethyl acetate (257 mL) separately at reflux temperature, and added slowly to the solution of tamsulosin at 40-45° C. The mixture was stirred at reflux temperature for 20 mins, then cooled to room temperature and stirred for 2 hrs. The precipitate was filtered under vacuum, washed with ethyl acetate (20 mL) and the off white solid was collected and dried in hot air oven at 60° C. for 3 hrs to afford 10 gm of (R)-tamsulosin maleate salt. Melting range 128.4-131.3° C., and chemical purity by HPLC: 98.14% and 100% of (R)-tamsulosin maleate salt (chiral HPLC). DSC: 113.3-120.9° (peak 116.8°); XRD: 15.3, 23.9, 21.4, 18.6, 19.6, 23.1, 14.6 and 22.8 (2 theta values in decreasing order of intensity).

(d) R-Tamsulosin Tartrate Salt (R)-Tamsulosin free base (3.5 gm, 8.57 mmol) was dissolved in ethyl acetate (150 mL) at reflux temperature. (+)-Tartaric acid (0.65 gm, 4.33 mmol) was dissolved in ethyl acetate (100 mL) separately at reflux temperature and added slowly to the solution of tamsulosin at 40-45° C. The mixture was stirred at reflux temperature for 20 minutes, then cooled to room temperature and stirred for 2 hrs. The precipitate was filtered under vacuum, washed with ethyl acetate (15 mL), the off white sold collected and dried in hot air oven at 60° C. to afford 3.3 gm of (R)-tamsulosin (+)-tartrate salt of melting range 179.5-182.7° C., chemical purity by HPLC: 99.93% and 100% of (R)-tamsulosin (+) tartrate salt (chiral HPLC). DSC: 179-180.7° (sharp); XRD: 14.9, 11.5, 22.2, 25.3, 20.4, 19.3, 22.9, 20.1, 25.9 & 10.2 (2 theta values in decreasing order of intensity).

ADVANTAGES OF THE PRESENT INVENTION

Advantages of at least some embodiments of the present invention over the prior art, include, but are not limited to:
- Resolution of racemic tamsulosin is achieved with high enantiomeric excess (ee) with a single resolution.
- Both racemic tamsulosin free base and its salts can be directly employed for resolution with either of the resolving agents.
- The resolving agents are recoverable and reusable thereby making the process economical.
- The chirally pure R or S tamsulosin free bases or their salts of greater than 99% ee can be prepared for use in pharmaceutical compositions.
- Higher purities of the hydrochloride salt are easily achieved from the free base of 99% ee without further purification.
- The invention results in novel isomers and their salts.

While the invention has been described in detail and with reference to specific examples thereof, it will be apparent to one skilled in the art that various changes and modifications can be made therein without departing from the spirit and scope thereof.

What is claimed is:

1. A process to obtain solid R-tamsulosin free base or a salt the thereof, said process comprising the steps of:
   (a) mixing a racemic mixture of tamsulosin or salts thereof and S-BPA in a medium comprising an organic solvent and optionally water to provide a first mixture;
   (b) maintaining the first mixture at a temperature from 20° to 60° C. for a period from 2 to 10 hours to provide a second mixture comprising solid R-tamsulosin-S-BPA salt;
   (c) filtering the second mixture to obtain the solid R-tamsulosin-S-BPA salt;
   (d) basifying the solid R-tamsulosin-S-BPA salt to provide a third mixture comprising R-tamsulosin free base;
   (e) isolating the solid R-tamsulosin free base from the third mixture by extraction with at least one organic solvent and then removing the at least one organic solvent; and optionally
   (f) converting the R-tamsulosin free base to a pharmaceutically acceptable salt;
   (g) recovering the S-tamsulosin or a salt thereof from a filtrate obtained in step (c) above; and
   (h) recovering the S-BPA chiral resolving agent used in the process from mother liquors obtained in steps (e) or (g).

2. The process of claim 1, wherein a base used for decomposing the solid R-tamsulosin-S-BPA salt in the basifying step is at least one of an alkali hydroxide and an alkali carbonate.

3. The process of claim 1, wherein a base used for decomposing the solid R-tamsulosin-S-BPA salt in the basifying step is ammonium hydroxide.

4. The process of claim 1, wherein the organic solvent of the medium is at least one member selected from the group consisting of ethers, esters, hydrocarbons, nitriles and ketones.

5. The process of claim 1, wherein the organic solvent of the medium is acetone.

6. The process of claim 1, wherein the at least one organic solvent of step (e) is at least one member selected from the group consisting of ethers, esters and hydrocarbons.

7. The process of claim 1, wherein the at least one organic solvent of step (e) is ethyl acetate.

8. The process of claim 1, wherein the racemic mixture is a salt of tamsulosin selected from the group consisting of oxalate, fumarate, maleate, salicylate and tartrate.

9. The process of claim 1, wherein:
   a base used for decomposing the solid R-tamsulosin-S-BPA salt in the basifying step is at least one of ammonium hydroxide, an alkali hydroxide and an alkali carbonate;
   the organic solvent of the medium is at least one member selected from the group consisting of ethers, esters, hydrocarbons, nitriles and ketones;
   the at least one organic solvent of step (e) is at least one member selected from the group consisting of ethers, esters and hydrocarbons; and
   the racemic mixture comprises tamsulosin and/or a salt of tamsulosin selected from the group consisting of oxalate, fumarate, maleate, salicylate and tartrate.

10. A process for resolving a racemic mixture of (R) and (S) isomers of tamsulosin or a salt thereof, said process comprising:
   (a) mixing a racemic mixture of tamsulosin or salts thereof and R-BPA in a medium comprising an organic solvent and optionally water to provide a first mixture;
   (b) maintaining the first mixture at a temperature from 20° to 60° C. for a period from 2 to 10 hours to provide a second mixture comprising solid S-tamsulosin-R-BPA salt;
   (c) filtering the second mixture to obtain the solid S-tamsulosin-R-BPA salt;
   (d) basifying the solid S-tamsulosin-R-BPA salt to provide a third mixture comprising S-tamsulosin free base;
   (e) isolating the solid S-tamsulosin free base from the third mixture by extraction with at least one organic solvent and then removing the at least one organic solvent; and optionally
   (f) converting the S-tamsulosin free base to a pharmaceutically acceptable salt;
   (g) recovering the R-tamsulosin or a salt thereof from a filtrate obtained in step (c) above; and
   (h) recovering the R-BPA chiral resolving agent used in the process from mother liquors obtained in steps (e) or (g).

11. The process of claim 10, wherein a base used for decomposing the solid S-tamsulosin-R-BPA salt in the basifying step is at least one of an alkali hydroxide and an alkali carbonate.

12. The process of claim 10, wherein a base used for decomposing the solid R-tamsulosin-S-BPA salt in the basifying step is ammonium hydroxide.

13. The process of claim 10, wherein the organic solvent of the medium is at least one member selected from the group consisting of ethers, esters, hydrocarbons, nitriles and ketones.

14. The process of claim 10, wherein the organic solvent of the medium is acetone.

15. The process of claim 10, wherein the at least one organic solvent of step (e) is at least one member selected from the group consisting of ethers, esters and hydrocarbons.

16. The process of claim 10, wherein the at least one organic solvent of step (e) is ethyl acetate.

17. The process of claim 10, wherein the racemic mixture is a salt of tamsulosin selected from the group consisting of oxalate, fumarate, maleate, salicylate and tartrate.

18. The process of claim 10, wherein:
- a base used for decomposing the solid S-tamsulosin-R-BPA salt in the basifying step is at least one of ammonium hydroxide, an alkali hydroxide and an alkali carbonate;
- the organic solvent of the medium is at least one member selected from the group consisting of ethers, esters, hydrocarbons, nitriles and ketones;
- the at least one organic solvent of step (e) is at least one member selected from the group consisting of ethers, esters and hydrocarbons; and
- the racemic mixture comprises tamsulosin and/or a salt of tamsulosin selected from the group consisting of oxalate, fumarate, maleate, salicylate and tartrate.

19. A process for preparing R-tamsulosin-S-BPA salt, said process comprising:
- (a) mixing a racemic mixture of tamsulosin or salts thereof and S-BPA in a medium comprising an organic solvent and optionally water to provide a first mixture;
- (b) maintaining the first mixture at a temperature from 20° to 60° C. for a period from 2 to 10 hours to provide a second mixture comprising solid R-tamsulosin-S-BPA salt; and
- (c) filtering the second mixture to obtain the solid R-tamsulosin-S-BPA salt.

20. A process for preparing S-tamsulosin-R-BPA salt, said process compnsing:
- (a) mixing a racemic mixture of tamsulosin or salts thereof and R-BPA in a medium comprising an organic solvent and optionally water to provide a first mixture;
- (b) maintaining the first mixture at a temperature from 20° to 60° C. for a period from 2 to 10 hours to provide a second mixture comprising solid S-tamsulosin-R-BPA salt; and
- (c) filtering the second mixture to obtain the solid S-tamsulosin-R-BPA salt.

* * * * *